US011345918B2

(12) United States Patent
Faucher et al.

(10) Patent No.: US 11,345,918 B2
(45) Date of Patent: May 31, 2022

(54) APTAMERS BINDING TO LEGIONELLA PNEUMOPHILA

(71) Applicant: THE ROYAL INSTITUTION FOR THE ADVANCEMENT OF LEARNING/MCGILL UNIVERSITY, Montreal (CA)

(72) Inventors: Sebastien Faucher, Vaudreuil-Dorion (CA); Mariam Saad, Montreal (CA); Maryam Tabrizian, Longueuil (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

(21) Appl. No.: 16/850,355

(22) Filed: Apr. 16, 2020

(65) Prior Publication Data

US 2020/0354722 A1 Nov. 12, 2020

Related U.S. Application Data

(60) Provisional application No. 62/845,508, filed on May 9, 2019.

(51) Int. Cl.

*C12N 15/115* (2010.01)
*C12Q 1/6825* (2018.01)
*C12Q 1/689* (2018.01)

(52) U.S. Cl.

CPC ............ *C12N 15/115* (2013.01); *C12Q 1/689* (2013.01); *C12Q 1/6825* (2013.01); *C12N 2310/16* (2013.01); *C12Q 2565/607* (2013.01); *C12Q 2565/626* (2013.01)

(58) Field of Classification Search

None

See application file for complete search history.

(56) References Cited

U.S. PATENT DOCUMENTS

2016/0251703 A1* 9/2016 Gilboa-Geffen ..... C12Q 1/6818 506/1

FOREIGN PATENT DOCUMENTS

RU 2737829 C1 * 3/2020

OTHER PUBLICATIONS

Machine English translation of RU 2737829 on Jun. 8, 21, pp. 1-35 (Year: 2021).*

Eurostars Cut-off 7 Project: Portable aptamer biosensors for the detection of pathogens, retrieved on line, https://www.era-learn.eu/network-information/networks/eurostars/cut-off-13-3-2014/portable-aptamer-biosensors-for-the-detection-of-pathogens-on-the-spot-legionella-amoeba-complex, pp. 1-4 (Year: 2016).*

Berger, K. H. and R. R. Isberg (1993). "Two distinct defects in intracellular growth complemented by a single genetic locus in Legionella pneumophila." Molecular Microbiology 7(1): 7-19.

Chang, Y.-C., C.-Y. Yang, R.-L. Sun, Y.-F. Cheng, W.-C. Kao and P.-C. Yang (2013). "Rapid single cell detection of *Staphylococcus aureus* by aptamer-conjugated gold nanoparticles." Scientific reports 3: 1863.

Hovel-Miner, G., S. Pampou, S. P. Faucher, M. Clarke, I. Morozova, P. Morozov, J. J. Russo, H. A. Shuman and S. Kalachikov (2009). "δ(S) Controls Multiple Pathways Associated with Intracellular Multiplication of Legionella pneumophila." Journal of Bacteriology 191(8): 2461-2473.

Kim, Yeon Seok, Min Young Song, Jongsoo Jurng, and Byoung Chan Kim. 2013. 'Isolation and characterization of DNA aptamers against *Escherichia coli* using a bacterial cell—systematic evolution of ligands by exponential enrichment approach', Analytical biochemistry, 436: 22-28.

Lévesque, S., C. Lalancette, K. Bernard, A. L. Pacheco, R. Dion, J. Longtin and C. Tremblay (2016). "Molecular Typing of Legionella pneumophila Isolates in the Province of Quebec from 2005 to 2015." PloS one 11(10): e0163818.

Li, L., N. Mendis, H. Trigui and S. P. Faucher (2015). "Transcriptomic changes of Legionella pneumophila in water." BMC genomics 16(1): 637.

Mendis, N., P. McBride and S. P. Faucher (2015). "Short-term and long-term survival and virulence of Legionella pneumophila in the defined freshwater medium Fraquil." PloS one 10(9): e0139277.

Morel, F. M., J. C. Westall, J. Reuter and J. P. Chaplick (1975). Description of the algal growth media 'Aquil'and 'Fraquil'. Water Quality Laboratory, Ralph Parsons Laboratory for Water Resources and Hydrodynamics, Massachusetts Institute of Technology, Technical Report 16.

(Continued)

*Primary Examiner* — Brian Whiteman

(74) *Attorney, Agent, or Firm* — Christian Cawthorn; Norton Rose Fulbright Canada LLP

(57) ABSTRACT

The present disclosure concerns aptamers which specifically bind to *Legionella pneumophila* which can be used to detect the presence of *Legionella pneumophila* in a sample.

18 Claims, 20 Drawing Sheets

Specification includes a Sequence Listing.

(56) References Cited

OTHER PUBLICATIONS

Schutze, T., B. Wilhelm, N. Greiner, H. Braun, F. Peter, M. Mori, V. A. Erdmann, H. Lehrach, Z. Konthur, M. Menger, P. F. Arndt and J. Glokler (2011). "Probing the SELEX process with next-generation sequencing." PLoS One 6(12): e29604.
Song, M.-S., S. S. Sekhon, W.-R. Shin, H. C. Kim, J. Min, J.-Y. Ahn and Y.-H. Kim (2017). "Detecting and discriminating shigella sonnei using an aptamer-based fluorescent biosensor platform " Molecules 22(5): 825.
Stoltenburg, R. and B. Strehlitz (2018). "Refining the Results of a Classical SELEX Experiment by Expanding the Sequence Data Set of an Aptamer Pool Selected for Protein A." International Journal of Molecular Sciences 19(2): 642.
Zhou, J. and J. Rossi (2017). "Aptamers as targeted therapeutics: current potential and challenges." Nature Reviews Drug Discovery 16: 440.
Zuker M. Mfold web server for nucleic acid folding and hybridization prediction. Nucleic Acids Res. Jul. 1, 2003;31 (13):3406-15.

* cited by examiner

R10C1

(SEQ ID NO: 15)

R10C5

(SEQ ID NO: 14)

APTAMERS BINDING TO LEGIONELLA PNEUMOPHILA

CROSS-REFERENCE TO RELATED APPLICATIONS AND DOCUMENTS

The present application claims priority from U.S. provisional applications 62/835,730 filed on Apr. 18, 2019 and 62/845,508 filed on May 9, 2019 and both incorporated herein in their entirety. The present application also includes a sequence listing entitled USPTO_-_Sequence_Listing.txt also incorporated herein in its entirety.

TECHNOLOGICAL FIELD

The present disclosure concerns aptamers capable of specifically binding to *Legionella pneumophila.*

BACKGROUND

*Legionella pneumophila* (Lp) is a pathogenic Gram-negative bacterium responsible for two types of respiratory diseases, namely the severe pneumonia Legionnaires' Disease (LD) and the milder flu-like Pontiac fever. Lp occurs in both natural and engineered water systems and is one of the most prevalent pathogens in man-made, engineered water systems. Infections occur when the bacteria are aerosolized, and the contaminated aerosols are inhaled; Lp can then infects and replicates in alveolar macrophages. Modern water systems provide optimal transmission conditions for Lp by generating aerosols. Leading sources of infection are cooling towers, hot water distribution systems, humidifiers, misters, showers, fountains, spa pools and evaporative condensers.

Outbreaks of LD consistently occur globally and have increased in recent years. The average incidence rate is about 10-15 cases per million people. According to the Centre for Disease Control (CDC-USA), incidences of legionellosis have increased by four and a half times between 2000 and 2016. Similarly, the Public Health Agency of Canada (PHAC) reported a 106% increase between the years 2006 and 2016.

The rise in LD outbreaks can be attributed to several factors such as aging infrastructures and an aging population who is more vulnerable to such infections, as well as increases in diagnosis and reporting. Nevertheless, most LD outbreaks are the consequences of management failure of man-made water systems. Examples of these failures for water distribution systems include keeping the temperature of hot water distribution system below 50° C. and allowing water to stagnate. For cooling towers, lack of regular cleaning and disinfection is associated with increased risk. In both cases, routine monitoring of Lp is critical to evaluate risk, initiate treatment of water systems, and prevent outbreaks. The European Center of Disease Control (ECDC) specifies that immediate corrective measures should be taken when Lp level reach a value of 10,000 CFU/L.

Currently, there are two ISO-certified strategies to detect Lp from water systems: the standard plate count method (AFNOR NF T90-431, ISO 11731) and qPCR (AFNOR NF T90-471, ISO/TS 12869)(ISO 2017). The plate count method is the gold standard for detecting Lp and involves its cultivation on selective media and the enumeration of bacterial colonies showing Lp-specific morphology. The whole procedure takes up to 14 days which delays the application of disinfectant and increase the chances of outbreak. A pilot study evaluated the consistency of the results obtained by this method between several different laboratories. Qualitative results did not differ drastically between laboratories, but quantitative results showed large variation, within and between laboratories. Therefore, the culture method should be use with caution to precisely enumerate Lp. A second major limitation is the presence of viable but non-culturable (VBNC) Lp cells which lead to underestimation of the true amount of infectious Lp in a system. The qPCR method relies on the quantification of *Legionella* DNA. Its major advantages in comparison with conventional culture method is the rapid turn-around time, high sensitivity and specificity, low limit of detection, as well as the ability to detect VBNC cells. When used in conjunction with the culture method, qPCR can serve as a powerful tool. There are, however, several drawbacks: qPCR typically overestimates Lp burden because it detects dead cells and the presence of PCR inhibitors may prevent the use of this method. In addition, multiple processing steps are required which increases the overall cost of the qPCR method.

It would be highly desirable to be provided with a biosensor to quantify in real-time and with high sensitivity the presence of Lp in a fluid, such as water, air or a biological sample.

BRIEF SUMMARY

The present disclosure concerns aptamers which specifically bind to *Legionella pneumophila* (Lp) which can be used to detect the presence of *Legionella pneumophila* in a sample.

In a first aspect, the present disclosure describes an aptamer specific for *Legionella pneumophila*, and having: at least about 15 nucleotides; and a dissociation constant with *Legionella pneumophila* between about 1 and 1000 nM. In an embodiment, the aptamer comprises a core nucleic acid molecule having the nucleic acid sequence of SEQ ID NO: 16, being a variant of the nucleic acid sequence of SEQ ID NO: 16 or being a fragment of the nucleic acid sequence of SEQ ID NO: 16. In another embodiment, the aptamer further comprises a 5' wing nucleic acid molecule covalently associated with the 5' end of the core nucleic acid molecule, wherein the 5' wing nucleic acid molecule has the nucleic acid sequence of SEQ ID NO: 1, is a variant of the nucleic acid sequence of SEQ ID NO: 1 or is a fragment of the nucleic acid sequence of SEQ ID NO: 1. In yet another embodiment, the aptamer further comprises a 3' wing nucleic acid molecule covalently associated with the 3' end of the core nucleic acid molecule, wherein the 3' wing nucleic acid molecule has the nucleic acid sequence of SEQ ID NO: 2, is a variant of the nucleic acid sequence of SEQ ID NO: 2 or is a fragment of the nucleic acid sequence of SEQ ID NO: 2. In still another embodiment, the aptamer comprises the nucleic acid sequence of SEQ ID NO: 14, is a variant of the nucleic acid sequence of SEQ ID NO: 14 or is a fragment of the nucleic acid sequence of SEQ ID NO: 14. In yet another embodiment, the aptamer comprises a core nucleic acid molecule and having the nucleic acid sequence of SEQ ID NO: 17, being a variant of the nucleic acid sequence of SEQ ID NO: 17 or being a fragment of the nucleic acid sequence of SEQ ID NO: 17. In still another embodiment, the aptamer further comprises a 5' wing nucleic acid molecule covalently associated with the 5' end of the core nucleic acid molecule, wherein the 5' wing nucleic acid molecule has the nucleic acid sequence of SEQ ID NO: 1, is a variant of the nucleic acid sequence of SEQ ID NO: 1 or is a fragment of the nucleic acid sequence of SEQ ID NO: 1. In yet another embodiment, the aptamer further comprises a 3' wing nucleic acid molecule covalently associated with the 3' end of the core nucleic acid molecule, wherein the 3' wing nucleic acid molecule has the nucleic acid sequence of SEQ ID NO: 2, is a variant of the nucleic acid sequence of SEQ ID NO: 2 or is a fragment of the nucleic acid sequence of SEQ ID NO: 2. In another embodiment, the aptamer comprises the nucleic acid sequence of SEQ ID NO: 15, is a variant of the nucleic acid sequence of SEQ ID NO: 15 or is a fragment of the nucleic acid sequence of SEQ ID NO: 15. In some embodiments, the aptamer is attached to a detectable moiety. In other embodiments, the aptamer is attached to a surface of a material or a sensor.

According to a second aspect, the present disclosure provides a solid support comprising a surface, wherein the surface is attached to the aptamer described herein.

According to a third aspect, the present disclosure provides a sensor comprising a surface, wherein the surface is attached to the aptamer described herein.

According to a fourth aspect, the present disclosure provides a method for detecting the presence of *Legionella pneumophila* in a sample. The method comprises (i) contacting the aptamer described herein, the material described herein or the sensor described herein with the sample to provide a mixture, (ii) determining the presence of a complex between *Legionella pneumophila* and the aptamer, the material or the sensor in the mixture and (iii) characterizing the sample as comprising *Legionella pneumophila* if the complex is determined to be present in the mixture. In an embodiment, the sample is a water sample, a gaseous sample or a biological sample. In yet another embodiment, the aptamer is associated with a chromogenic label and step (ii) comprises performing colorimetry for determining the presence of the complex. In still a further embodiment, the aptamer is associated with a fluorescent label and step (ii) comprises performing a fluorescent-based assay for determining the presence of the complex. In some embodiments, the fluorescent-based assay is flow cytometry and/or microscopy. In still another embodiment, the aptamer is associated with a radioactive label and step (ii) comprises performing a radioactive-based assay for determining the presence of the complex. In still another embodiment, the method further comprises determining the viability of *Legionella pneumophila* in the sample.

BRIEF DESCRIPTION OF THE DRAWINGS

Having thus generally described the nature of the invention, reference will now be made to the accompanying drawings, showing by way of illustration, a preferred embodiment thereof, and in which.

LMG1794 by fluorescence microscopy. Binding to Lp strains lp120292 serves as a positive control. The no cells control consists of aptamer alone. Results are shown in brightfield and fluorescence in the absence of aptamers (No aptamer), the R10C5 aptamer (R10C5) and the R10C1 aptamer (R10C1).

Figure 7A:
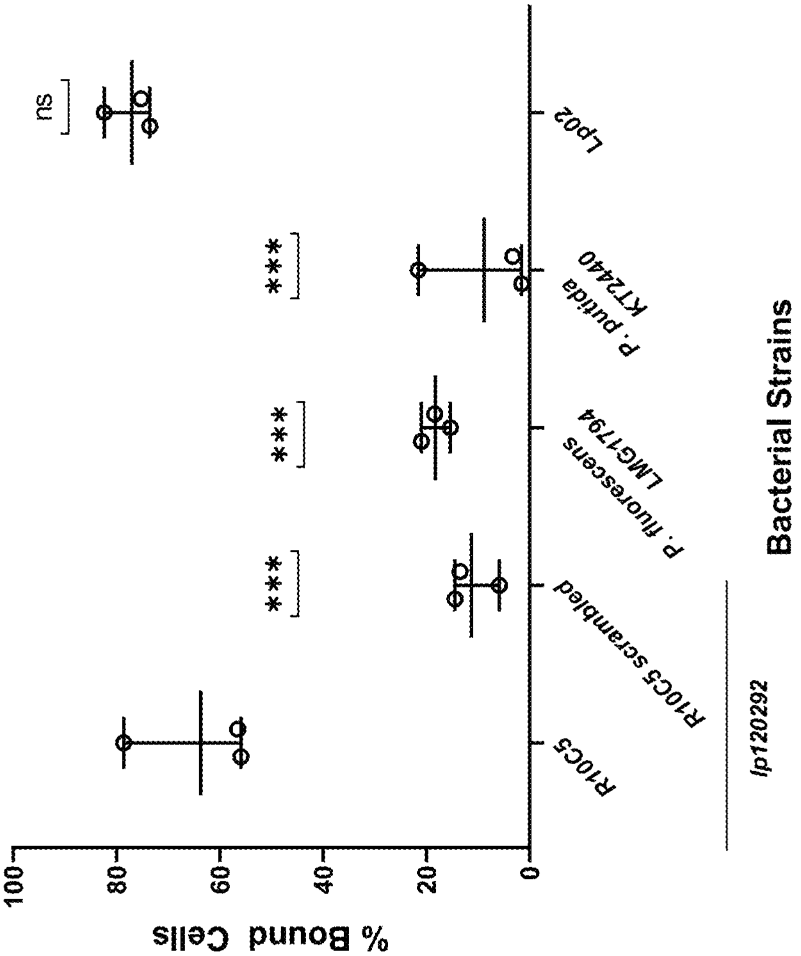

FIG. 7A shows percentage of cells bound by the R10C5 aptamer or a scrambled aptamer to *P. fluorescens, P. putida* or Lp strain Lp02 as analyzed by flow cytometry. The values of three experiments are shown with the mean and standard deviation. A one-way ANOVA with a Dunnett correction for multiple comparisons was used to infer statistical significance compared to Lp strain lp120292: *** $P<0.001$; ns, not significant.

Figure 7B:
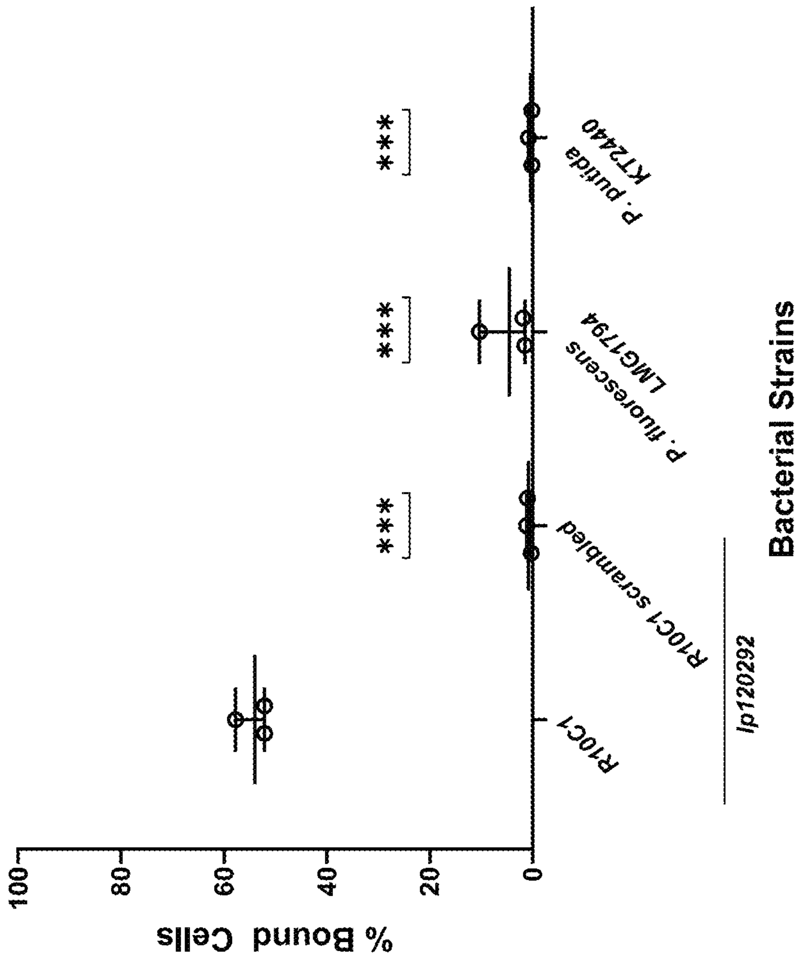

FIG. 7B shows percentage of cells bound by the R10C1 aptamer or a scrambled aptamer to *P. fluorescens, P. putida* or Lp strain Lp02 as analyzed by flow cytometry. The values of three experiments are shown with the mean and standard deviation. A one-way ANOVA with a Dunnett correction for multiple comparisons was used to infer statistical significance compared to Lp strain lp120292: *** $P<0.001$; ns, not significant.

Figure 7C:
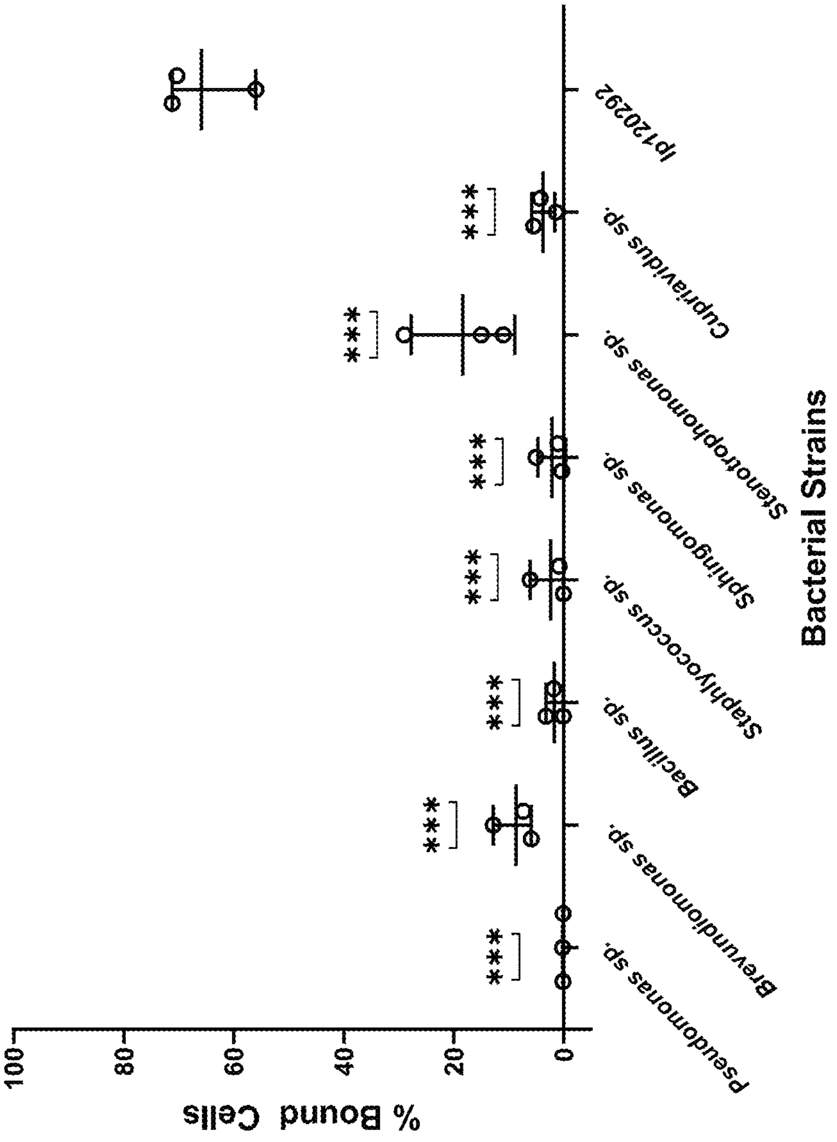

FIG. 7C shows percentage of cells bound by the R10C5 aptamer to various environmental isolated as analyzed by flow cytometry. The values of three experiments are shown with the mean and standard deviation. A one-way ANOVA with a Dunnett correction for multiple comparisons was used to infer statistical significance compared to Lp strain lp120292: *** $P<0.001$; ns, not significant.

Figure 7D:
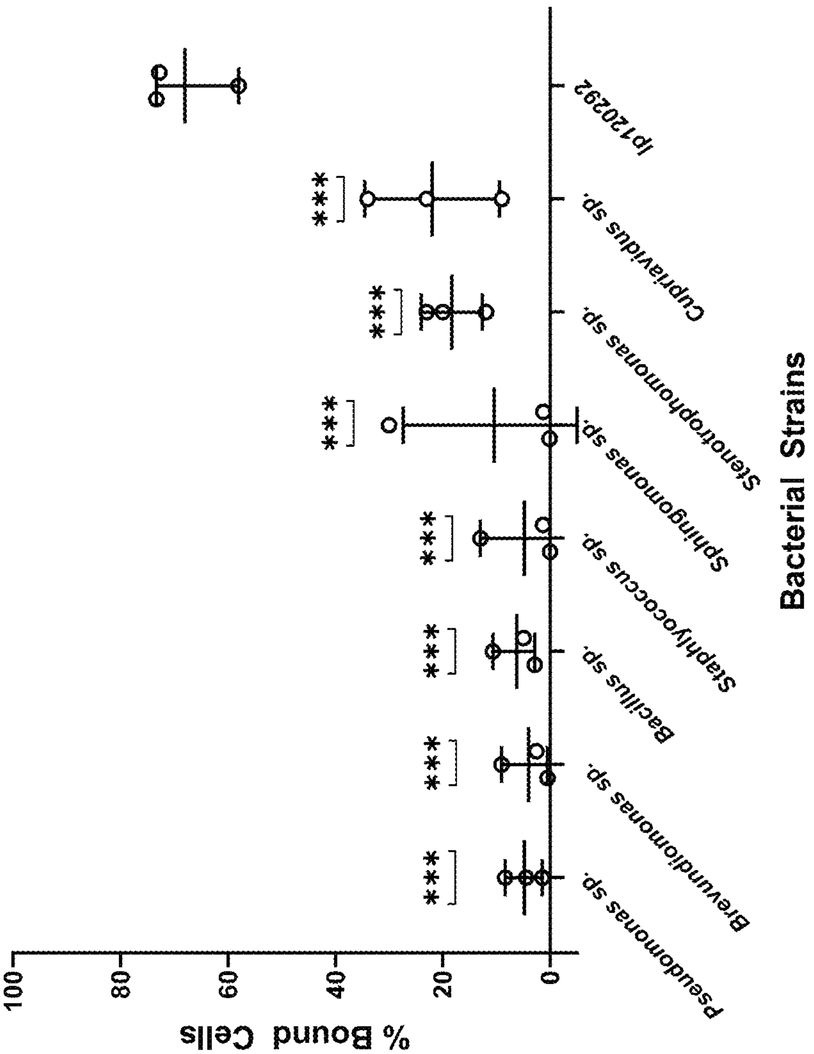

FIG. 7D shows percentage of cells bound by the R10C1 aptamer to various environmental isolated as analyzed by flow cytometry. The values of three experiments are shown with the mean and standard deviation. A one-way ANOVA with a Dunnett correction for multiple comparisons was used to infer statistical significance compared to Lp strain lp120292: *** $P<0.001$; ns, not significant.

Figure 8A:
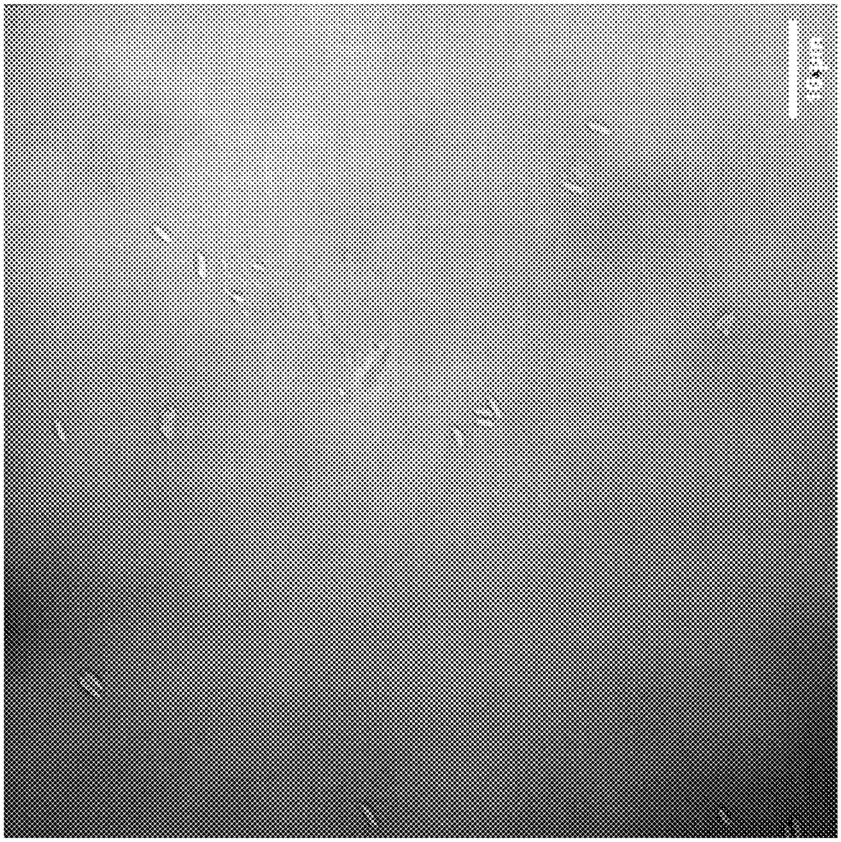

FIG. 8A shows the fluorescence of Lp strains lp120292 in the absence of an aptamer. Scale bar=10 μM.

Figure 8B:
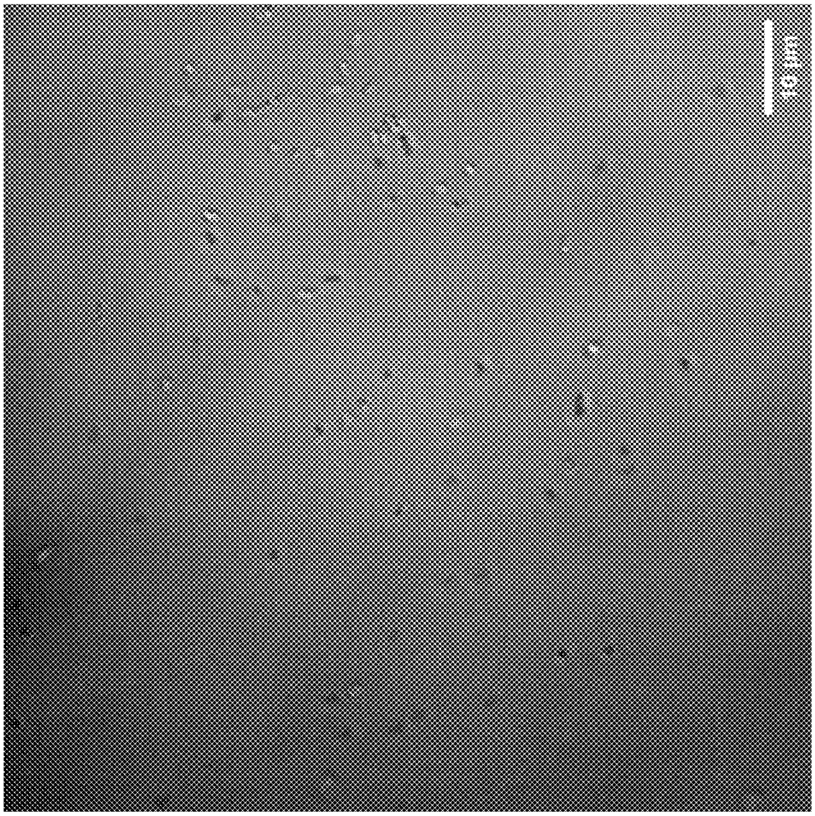

FIG. 8B shows the fluorescence of *P. fluorescens* LMG1794 in the absence of an aptamer. Scale bar=10 μM.

Figure 8C:
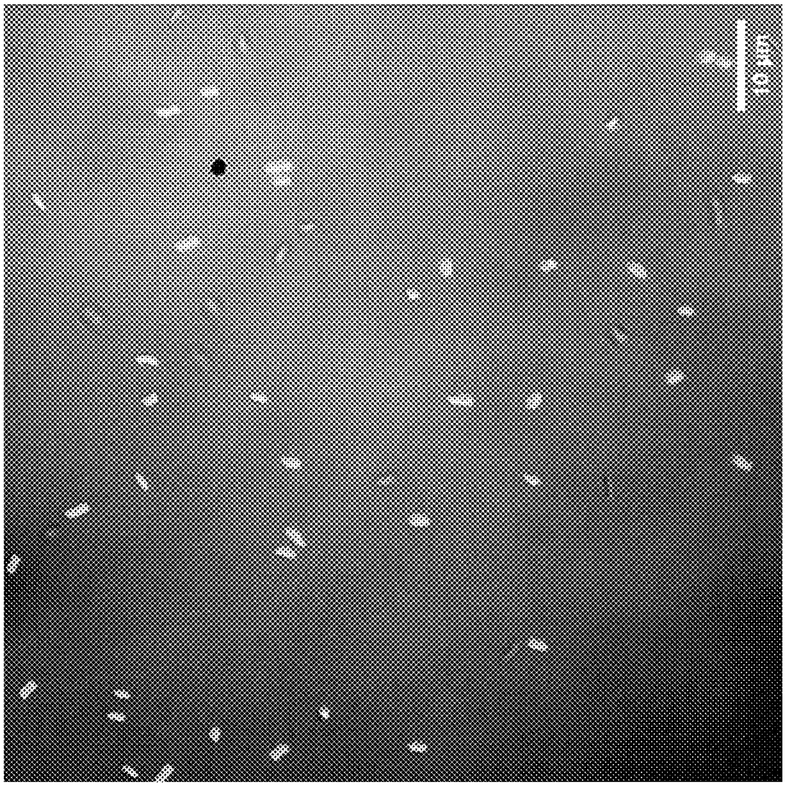

FIG. 8C shows the fluorescence of Lp strains lp120292 in the presence of the R10C5 aptamer. Scale bar=10 μM.

Figure 8D:
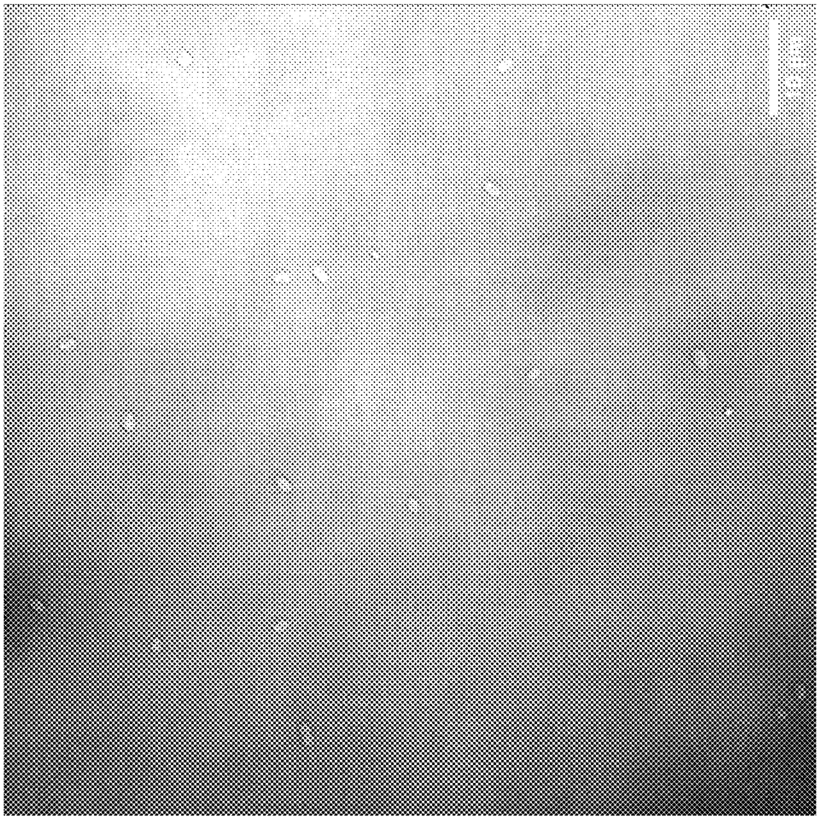

FIG. 8D shows the fluorescence of *P. fluorescens* LMG1794 in the R10C5 aptamer. Scale bar=10 μM.

Figure 8E:

FIG. 8E shows the fluorescence of Lp strains lp120292 in the presence of the R10C1 aptamer. Scale bar=10 μM.

Figure 8F:
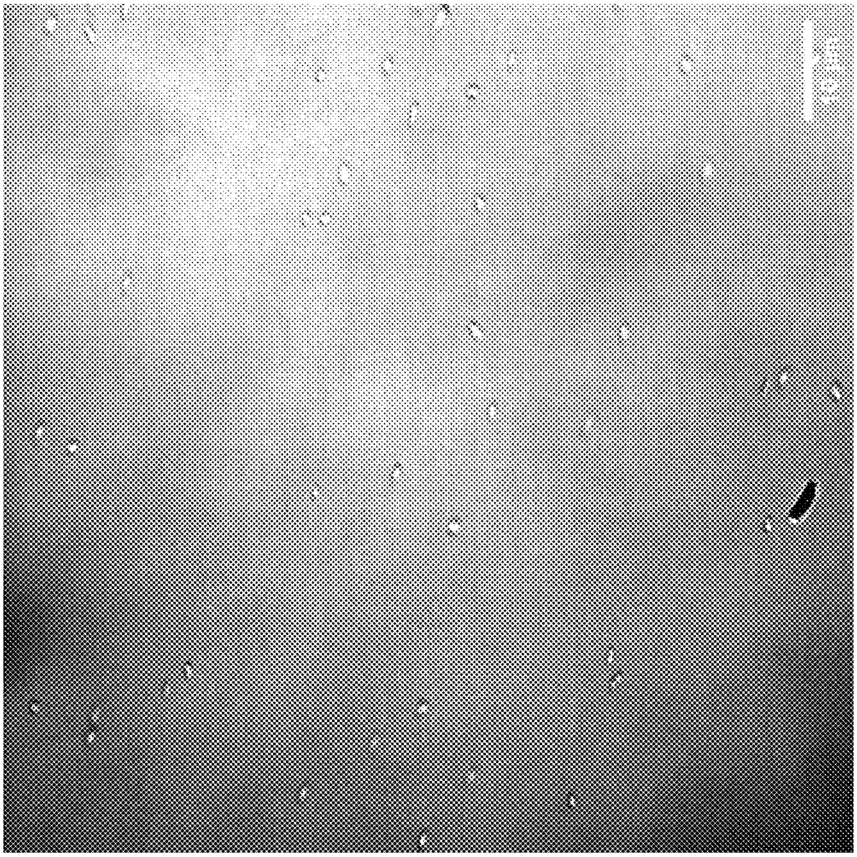

FIG. 8F shows the fluorescence of *P. fluorescens* LMG1794 in the R10C1 aptamer. Scale bar=10 μM.

DETAILED DESCRIPTION

Biorecognition elements, such as antibodies, can be used to detect *Legionella pneumophila*. Aptamers are becoming the primary choice for biosensing strategies due to their easily modifiable nature and versatility. Aptamers are antibody analogues composed of short single stranded DNA or RNA oligonucleotide that can be cost effectively synthesized in a high throughput manner. The aptamer folds into a specific, stable structure and interacts with its targets via shape complementarity, hydrogen bonding, electrostatic interactions and stacking interactions. This allows its binding with high affinity and specificity to a wide variety of targets ranging from small molecules, peptides, proteins to whole cells. A key characteristic of aptamers is the possibility to generate them in vitro in the same condition as those used for detecting the analyte. This is a clear advantage over antibodies which are produced under strict physiological conditions. In addition, aptamers can be easily modified and therefore be optimized for various sensing platforms such as lateral flow assays, Surface Plasmon Resonance (SPR) sensors, flow cytometry or fluorescence microscopy.

The procedure by which an aptamer can be created is known as Systemic Evolution of Ligands through EXponential enrichment (SELEX). SELEX is an iterative process which involves incubating a target with a large library of oligonucleotides, separating the target bound and unbound oligonucleotides and then amplifying the target bound sequences via PCR for the next round of selection. The selection rounds are repeated until the oligonucleotide pool is enriched with sequences that bind specifically and with high affinity to the target. Over the years, many variations of the original SELEX methods were published. Among those, Cell-SELEX can be used to select aptamers binding to whole living cells and, thus, eliminates the need for prior knowledge of a target molecule. Rounds of counter-selection are typically used to reduce aptamer cross-reactivity across targets by eliminating non-specific aptamers. Several of these aptamers are used in conjunction with optical, mechanical or electrical/electrochemical biosensors to mitigate the problems associated with traditional bacterial detection methods. Although numerous works have been done to detect *Legionella pneumophila* with the use of biosensors, no study has used or even created aptamers binding to Lp. Consequently, no aptamer and thus no aptamer-based technology currently exists for the detection of Lp.

Aptamers Specific for *Legionella pneumophila*

The present disclosure provides aptamers that specifically bind to (e.g., recognize) *Legionella pneumophila*. In the context of the present disclosure, the expressions "specific binding" or "specifically bind" refer to the interaction between two elements in a manner that is determinative of the presence of the elements in the presence or absence of a heterogeneous population of molecules. For example, under designated conditions, the aptamers of the present disclosure bind to *Legionella pneumophila* and do not bind in a significant manner to other bacteria (such as other *Legionella* sp. or other bacteria genus such as *Pseudomonas*). In some embodiments, the aptamers of the present disclosure do bind to other species of *Legionella* and/or to other bacterial genuses (like *Pseudomonas* sp., *Brevundiomonas* sp., *Bacillus* sp., *Staphlyococcus* sp. *Sphingomonas* sp., *Stenotrophomonas* sp. and/or *Cupriavidus* sp.) but only marginally.

The aptamers of the present disclosure are single-stranded molecules composed of deoxyribonucleic acid (DNA) nucleotides, ribonucleic acid (RNA) nucleotides or a combination of both deoxyribonucleic and ribonucleic acid nucleotides. In an embodiment, the aptamers of the present disclosure are exclusively made of deoxyribonucleic acid (DNA) nucleotides. The aptamers can be composed of naturally-occurring nucleotide bases (also referred to as bases), sugars and covalent internucleoside (backbone) linkages. The aptamers can also have "non-naturally-occurring" or "synthetic" portions which function similarly. In the context of the present disclosure, the term "nucleotides" refers to a deoxyribonucleic acid nucleotide or to a ribonucleic acid nucleotides.

The aptamers of the present disclosure can include various modifications, e.g., stabilizing modifications, and thus can include at least one modification in the phosphodiester linkage and/or on the sugar, and/or on the base. For example, the aptamer can include one or more phosphorothioate linkages, phosphorodithioate linkages, and/or methylphosphonate linkages. Different chemically compatible modified linkages can be combined, e.g., modifications where the synthesis conditions are chemically compatible. While modified linkages are useful, the aptamer can include phosphodiester linkages, e.g., include at least one phosphodiester linkage, or at least 5%, 10%, 20%, 30% or more phosphodiester linkages. Additional useful modifications include, without restriction, modifications at the 2'-position of the sugar (such as 2'-O-alkyl modifications, 2'-O-methyl modifications, 2'-amino modifications, 2'-halo modifications (e.g., 2'-fluoro) as well as acyclic nucleotide analogs. In another embodiment, the aptamer has modified linkages throughout, e.g., phosphorothioate; has a 3'- and/or 5'-cap; includes a terminal 3'-5' linkage. In some embodiments, the aptamer can be modified to bear a capturing moiety or signaling moiety, such as a fluorescent signaling moiety. The capturing/signaling moiety associated at any location on the aptamer as long as it does not interfere between the binding of the aptamer and Lp. In an embodiment, the capturing/signaling moiety is located at one or both ends of the aptamer. For example, the capturing/signaling moiety can be located at the 3' end, the 5' end or both at the 3' end at the 5' end of the aptamer. As such, the aptamer's 3' and/or 5' end can be modified to be associated with the capturing/signaling moiety.

In some embodiments, the aptamer includes a concatemer and comprises two or more oligonucleotide sequences joined by one or more linker. The linker may, for example, consist of modified nucleotides or non-nucleotide units. In some embodiments, the linker can provide flexibility to the aptamer. The use of concatemers as aptamers can provide a facile method to synthesize a final molecule, by joining smaller oligonucleotides building blocks to obtain the desired length. For example, a 12 carbon linker ($C_{12}$ phosphoramidite) can be used to join two or more concatemers and provide length, stability and flexibility.

The aptamers of the present disclosure can include a natural or a non-natural backbone. Non-natural or synthetic backbones include, for example, phosphorothioates, chiral phosphorothioates, phosphorodithioates, phosphotriesters aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, carboranyl phosphate and borano-phosphates having normal 3'-5' linkages, 2'-5' linked analogs of these, and those having inverted polarity wherein one or more internucleotide linkages is a 3' to 3', 5' to 5' or 2' to 2' linkage. Aptamers having inverted polarity typically include a single 3' to 3' linkage at the 3'-most internucleotide linkage i.e. a single inverted nucleoside residue which may be abasic (the nucleobase is missing or has a hydroxyl group in place thereof). Some exemplary modified aptamers' backbones that do not include a phosphodiester linkage have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Particularly advantageous are backbone linkages that include one or more charged moieties.

The aptamers of the present disclosure may also contain one or more substituted sugar moieties. For example, such oligonucleotides can include one of the following 2'-modifications: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to $C_{10}$ alkyl or $C_2$ to $C_{10}$ alkenyl and alkynyl, or 2'-O—(O-carboran-1-yl)methyl. Particular examples are $O[(CH_2)nO]_m$ $CH_3$, $O(CH_2)$~$OCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to 10. Other exemplary aptamers can include one of the following 2'-modifications: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$. $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl.

Other modifications to the aptamers include Locked Nucleic Acids (LNAs) in which the 2'-hydroxyl group is linked to the 3' or 4' carbon atom of the sugar ring thereby forming a bicyclic sugar moiety. Other modifications include 2'-methoxy (2'-O—$CH_3$), 2'-methoxyethyl (2'O—$CH_2$—$CH_3$), 2'-ethyl, 2'-ethoxy, 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F).

The 2'-modification may be in the arabino (up) position or ribo (down) position. Similar modifications may also be made at other positions on the aptamers, particularly the 3' position of the sugar on the 3' terminal nucleotide or in 2'-5' linked oligonucleotides and the 5' position of the 5' terminal nucleotide. The aptamers may also have sugar mimetics such as cyclobutyl moieties in place of the pentofuranosyl sugar.

The aptamers of the present disclosure can include "unmodified" or "natural" bases (nucleobases) such as adenine (A) and guanine (G), and the pyrimidine bases thymine (T), cytosine (C) and uracil (U). The aptamers may also include base modifications or substitutions. Modified bases include, but are not limited to other synthetic and naturally-occurring bases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified bases may also include those in which the purine or pyrimidine base is replaced with other heterocycles, for example 7-deaza-adenine, 7-deazaguanosine, 2-aminopyridine and 2-pyridone.

Another type of modification that can be included in the aptamers of the present disclosure are phosphorodithioate linkages. The aptamers comprising modified oligonucleotides containing phosphorothioate or dithioate linkages may also contain one or more substituted sugar moieties particularly modifications at the sugar moieties including, without restriction, 2'-ethyl, 2'-ethoxy, 2'-methoxy, 2'-aminopropoxy, 2'-allyl, 2'-fluoro, 2'-pentyl, 2'-propyl, 2'-dimethylaminooxyethoxy, and 2'-dimethylaminoethoxyethoxy. The 2'-modification may be in the arabino (up) position or ribo (down) position. A preferred 2'-arabino modification is 2'-fluoro. Similar modifications may also be made at other positions on the aptamer, particularly the 3' position of the sugar on the 3' terminal nucleotide or in 2 '-5' linked oligonucleotides and the 5' position of 5' terminal nucleotide.

Figure 3:
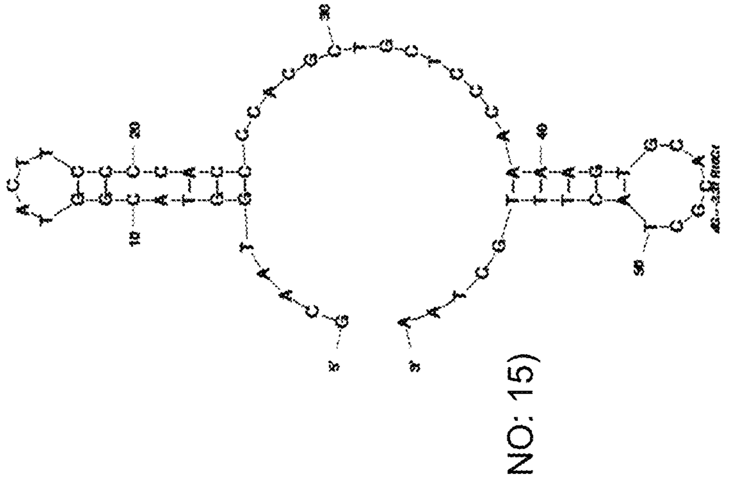
FIG. 3 shows proposed structures of the aptamers R10C5 (having the nucleotide sequence of SEQ ID NO: 14) and R10C1 (having the nucleotide sequence of SEQ ID NO: 15) were determined using the mfold webserver.
Figure 3:
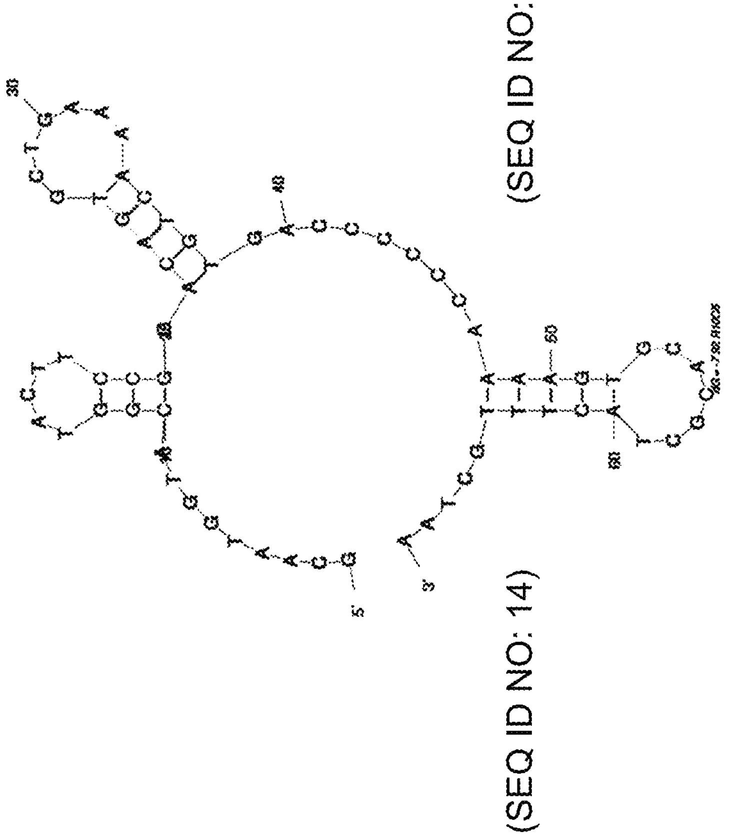

Even though the aptamers of the present disclosure are synthesized as single-stranded molecules they can, under the appropriate conditions (e.g., salt, pH, temperature), form a secondary "hairpin" structure. As shown in FIG. 3, the aptamers R10C5 and R10C1 forms a hairpin structure in which some stretches of the molecule are capable of base-pairing (e.g., capable of forming sections of double-stranded DNA and/or RNA) with other stretches of the molecule which are located several nucleotides upstream or downstream. As also shown in FIG. 3, the double-stranded configuration of R10C5 and R10C1 is not observed on the entire length of the molecule, but only in some regions. In some embodiments, the aptamers of the disclosure (which include R10C5 and R10C1) are also capable of forming a secondary "hairpin" structure which is substantially similar to the one shown on FIG. 3. The aptamer of the present disclosure forms a hairpin structure in which some stretches of the molecule are capable of base-pairing (e.g., capable of forming sections of double-stranded DNA and/or RNA) with other stretches of the molecule which may be located several nucleotides upstream or downstream. The double-stranded configuration of the aptamer of the present disclosure is not observed on the entire length of the molecule, but only in some regions.

In an embodiment in which the aptamer has the nucleic acid sequence of SEQ ID NO: 14, the aptamer can form at least one stretch (and in an embodiment, a combination of stretches) of double stranded DNA/RNA (which is also referred to as a stem structure) between the following positions:

- the nucleotides at positions 10 to 12 (CGG) of SEQ ID NO: 14 with the nucleotides at positions 18 to 20 (CCG) of SEQ ID NO: 14;
- the nucleotide at positions 22 to 26 (ACAGT) of SEQ ID NO: 14 with the nucleotides at positions 34 to 38 (ACTGT) of SEQ ID NO: 14; and/or
- the nucleotides at position 48 to 52 (AAAGT) of SEQ ID NO: 14 with the nucleotides at position 60 to 64 (ACTTT) of SEQ ID NO: 14.

In an embodiment in which the aptamer has the nucleic acid sequence of SEQ ID NO: 14, the aptamer can form at least one stretch (and in an embodiment, a combination of stretches) of single stranded DNA/RNA between the following positions:

- the nucleotides at positions 1 to 9 of SEQ ID NO: 14;
- the nucleotide at positions 13 to 17 of SEQ ID NO: 14 (which can form a bulge structure);
- the nucleotides at positions 20 and 21 of SEQ ID NO: 14;
- the nucleotide at positions 27 to 33 of SEQ ID NO: 14 (which can form a bulge structure);
- the nucleotides at positions 39 to 47 of SEQ ID NO: 14;
- the nucleotides at positions 53 to 59 (which can form a bulge structure); and/or
- the nucleotides at positions 65 to 69 of SEQ ID NO: 14.

In an embodiment in which the aptamer has the nucleic acid sequence of SEQ ID NO: 16, the aptamer can form at least one stretch (and in an embodiment, a combination of stretches) of double stranded DNA/RNA (which is also referred to as a stem structure) between the nucleotides as positions 3 to 7 (ACAGT) of SEQ ID NO: 16 with the nucleotides at positions 15 to 19 (ACTGT) of SEQ ID NO: 16.

In an embodiment in which the aptamer has the nucleic acid sequence of SEQ ID NO: 16, the aptamer can form at least one stretch (and in an embodiment, a combination of stretches) of single stranded DNA/RNA between the following positions:

- the nucleotides at positions 1 to 2 of SEQ ID NO: 16;
- the nucleotide at positions 8 to 14 of SEQ ID NO: 16 (which can form a bulge structure);
- the nucleotides at positions 20 to 26 of SEQ ID NO: 16; and/or
- the nucleotides at positions 53 to 59 (which can form a bulge structure).

In an embodiment in which the aptamer has the nucleic acid sequence of SEQ ID NO: 15, the aptamer can form at least one stretch (and in an embodiment, a combination of stretches) of double stranded DNA/RNA (which is also referred to as a stem structure) between the following positions:

- the nucleotides at positions 6 to 12 (GGTACGG) of SEQ ID NO: 15 with the nucleotides at positions 18 to 24 (CCCCACC) of SEQ ID NO: 15; and/or
- the nucleotides at position 39 to 43 (AAAGT) of SEQ ID NO: 15 with the nucleotides at position 51 to 55 (ACTTT) of SEQ ID NO: 15.

In an embodiment in which the aptamer has the nucleic acid sequence of SEQ ID NO: 15, the aptamer can form at least one stretch (and in an embodiment, a combination of stretches) of single stranded DNA/RNA between the following positions:

- the nucleotides at positions 1 to 5 of SEQ ID NO: 15;
- the nucleotides at positions 13 and 17 of SEQ ID NO: 15 (which can form a bulge structure);
- the nucleotides at positions 25 to 38 of SEQ ID NO: 15;
- the nucleotides at positions 44 to 50 of SEQ ID NO: 15 (which can form a bulge structure); and/or
- the nucleotides at positions 56 to 60 of SEQ ID NO: 15.

In an embodiment in which the aptamer has the nucleic acid sequence of SEQ ID NO: 17, the aptamer can form at least one stretch (and in an embodiment, a combination of stretches) of double stranded DNA/RNA (which is also referred to as a stem structure) between the nucleotides at positions 1 to 5 (CCACC) of SEQ ID NO: 17.

In an embodiment in which the aptamer has the nucleic acid sequence of SEQ ID NO: 17, the aptamer can form at least one stretch (and in an embodiment, a combination of stretches) of single stranded DNA/RNA between the nucleotides at positions 6 to 17 of SEQ ID NO: 17.

The aptamers of the present disclosure can be of the following formula:

5'-5W-C-3W-3' (I)

The structure of formula (I) comprises three main moieties: an optional 5' wing (referred to as "5W" in formula (I)), a core (referred to as "C" in formula (I)) and an optional 3' wing (referred to as "3W" in formula (I)). When the 5W moiety is present, the 3' end of the 5W section is associated (e.g., "—" which can be a covalent bond such as, for example, a nucleotide bond, a 5' to 3' nucleotide bond for example) to the 5' end of the C section of the aptamers of the present disclosure. When the 3W moiety is present, the 3' end of the C section is associated (e.g., "—" which can be a covalent bond such as, for example, a nucleotide bond, a 5' to 3' nucleotide bond for example) to the 5' end of the 3W section of the aptamers of the present disclosure. In some embodiments, the 3W section of the aptamers is absent.

The aptamers of the present disclosure are defined both by their nucleotide sequence, their physico-chemical properties and, in some embodiments, by their secondary structure. For example, some of the nucleotides of formula (I) are described of being capable of base pairing with another nucleotide. In the context of the present disclosure, a nucleotide is considered as "being capable of base pairing" with another nucleotide when they can form Watson-Crick base pairing. In such embodiment, C is considered of being capable of base pairing with G, G is considered of being capable of base pairing with C, A is considered of being capable of base pairing with T or U and T or U are considered of being capable of base pairing with A. Other nucleotides of formula (I) are described as not being able to base pair with another nucleotide. Still in the context of the present disclosure, a nucleotide is considered of "not being able to base pair" with another nucleotide when they cannot form Watson-Crick base pairing. For example, C is not able of base pairing with C, A, T or U, G is not able of base pairing with G, A, T or U, A is not able of base pairing with A, C or G, T is not able of base pairing with C, G, T or U and U is not able of base pairing with C, G, T or U.

At a minimum, the aptamers of the present disclosure include a core (C) moiety which has at least 15 consecutive nucleotides. In an embodiment, the aptamer of the present disclosure include a core structure having the nucleic acid sequence of SEQ ID NO: 16, being a variant of the nucleic acid sequence of SEQ ID NO: 16 or being a fragment of SEQ ID NO: 16. In some embodiments, the aptamers comprises, consists essentially of or consists of the nucleic acid sequence of SEQ ID NO: 16 or being a fragment of SEQ ID NO: 16. In another embodiment, the aptamer of the present disclosure include a core structure having the nucleic acid sequence of SEQ ID NO: 17, being a variant of the nucleic acid sequence of SEQ ID NO: 17 or being a fragment of SEQ ID NO: 17. In some embodiments, the aptamers comprises, consists essentially of or consists of the nucleic acid sequence of SEQ ID NO: 17 or being a fragment of SEQ ID NO: 17. In a further embodiment, the aptamer of the present disclosure include a core structure having the nucleic acid sequence of SEQ ID NO: 14, being a variant of the nucleic acid sequence of SEQ ID NO: 14 or being a fragment of SEQ ID NO: 14. In some embodiments, the aptamers comprises, consists essentially of or consists of the nucleic acid sequence of SEQ ID NO: 14 or being a fragment of SEQ ID NO: 14. In yet a further embodiment, the aptamer of the present disclosure include a core structure having the nucleic acid sequence of SEQ ID NO: 15, being a variant of the nucleic acid sequence of SEQ ID NO: 15 or being a fragment of SEQ ID NO: 15. In some embodiments, the aptamers comprises, consists essentially of or consists of the nucleic acid sequence of SEQ ID NO: 15 or being a fragment of SEQ ID NO: 15. In the context of the present disclosure, the expression "consists essentially of" or "consisting essentially of" refer to aptamers which include the nucleic acid sequence of SEQ ID NO: 16 or 17 but can also include, at their 5' or 3' end, additional nucleotides (e.g., for example up to 10 nucleotides) which do not increase or decrease the affinity and specificity of the aptamer for *Legionella pneumophila.*

The present disclosure thus provides variants of the aptamers of Formula (I), especially variants of aptamers having the nucleic acid sequence of any one of SEQ ID NO: 14 to 17, provided that such variants are capable of specifically binding to *Legionella pneumophila*. A "variant" of the aptamers of Formula (I) (also referred to as an aptamer variant) has at least one nucleotide addition or substitution when compared to the aptamers of Formula (I). The one or more added or substituted nucleotides that can be located anywhere in the molecule. The level of identity between the variants and the aptamers of Formula (I) is at least 70%, 75%, 80%, 85%, 90%, 95%, 96%, 97%, 98% or 99% over the entire length of the aptamers. In an embodiment, the variant aptamer has one or more of the stem and bulge structure as described herein. The aptamers having the variant nucleotide sequence of the present disclosure have at least about 15 nucleotides and a dissociation constant with *Legionella pneumophila* between about 1 and 1000 nM.

The present disclosure further provides fragments of the aptamers of Formula (I), including fragments of aptamers having the nucleic acid sequence of any one of SEQ ID NO: 14 to 17, and variants of the aptamers of Formula (I) provided that such fragments retain the ability to specifically bind to *Legionella pneumophila*. In some embodiments, the fragments of the aptamers of Formula (I) and of the aptamers of Formula (I) can exhibit some Lp binding activity. A "fragment" of the aptamers of Formula (I) (also referred to as an aptamer fragment) has at least one less nucleotide than the aptamers of Formula (I) or the variants described herein. The one or more nucleotides that can be removed from the aptamers of Formula (I) to provide the "fragments" can be located anywhere in the molecule. For example, the one or more nucleotide that can be removed from the aptamers of Formula (I) can be located, at the 5' end of the molecule, at the vicinity of the 5' end of the molecule, at the 3' end of the molecule and/or at the vicinity of the 3' end of the molecule. In an embodiment, the fragment is a 5'- and/or a 3'-end truncation of one or more nucleotides. In some embodiments, the fragments of the aptamers of Formula (I) have at least 10, 11, 12, 13, 14, 15, 16, 17, 18, 19, 20, 21, 22, 23, 24, 25, 26, 27, 28, 29, 30, 35, 40, 45, 50, 55, 60 or more contiguous nucleotides of the aptamers of Formula (I). In an embodiment, the aptamer fragment has one or more of the stem and bulge structure as described herein. The aptamers having the fragment nucleotide sequence of the present disclosure have at least about 15 nucleotides and a dissociation constant with *Legionella pneumophila* between about 1 and 1000 nM.

Methods of Using the *Legionella pneumophila*-Specific Aptamers

Since the aptamers of the present disclosure are able to specifically bind to *Legionella pneumophila*, they can be used to either detect the presence of Lp or purify Lp from a mixture comprising other components. In the methods using the aptamers of the present disclosure, a label (either covalently associated or non-covalently associated) is preferably used. In methods of detecting Lp, the label can be a detectable label (also referred to as a signaling moiety). Detectable labels include, but are not limited to, a radioactive label, an enzymatic label, a chromogenic label, a colorimetric, a fluorescent label, and a semiconductor label (such as quantum dots or gold nanoparticles). In methods of purifying Lp, the label can be an affinity label (also referred to as a capturing moiety). Affinity label systems include, but are not limited to, streptavidin/biotin system, digoxigenin (DIG)/anti-DIG antibody system, dinitrophenol (DNP)/anti-DNP system, etc. When the label is an affinity label, it is possible to use a magnetic bead system for recovering the aptamers (which may have bound to Lp) from the mixture.

In an embodiment, the Lp-specific aptamers are used in a method to detect the presence and optionally quantify the amount of Lp or localize Lp. For example, the Lp-specific aptamers can be used to detect the presence of Lp in a sample. In the context of the present disclosure, a sample is a mixture (either already in a liquid or capable of being provided as in a liquid form) suspected of comprising Lp. The sample can be a solution or a suspension. The sample can be a gaseous sample (e.g., air for example). The sample can be processed into a solution or a suspension. The sample can be a water sample. The water sample can be provided, for example, from a water system, such as a water distribution system (e.g., a plumbing system), a water cooling system (e.g., a cooling tower, an evaporative condenser, a humidifier, etc.), a water mist (e.g., from an air washer, a mist machine, a hot water heater, etc.), a hot water source (e.g., a spa, a spring, a shower, a fountain for example). The sample can be a biological sample. Exemplary biological samples include, but are not limited to, bodily fluids (e.g., blood, urine, gastro-intestinal juice, interstitial fluid, lachrymal fluid, sweat, saliva, stools, sputum, pus, cerebrospinal fluid, semen, prostatic fluid, milk, nipple aspirate fluid, lachrymal fluid, perspiration), tissues (swabs (e.g., cheek swabs), tissue biopsy), fractionated bodily fluids (serum, plasma, etc.), cell extracts (e.g., cytoplasmic membrane, mitochondrial extract, nuclear extracts, etc.), cell suspensions, secretions as well as cultures of such biological samples. The sample can be derived from a biofilm suspected of being formed, at least in part, by Lp, or a biofilm formed by other species and suspected of harboring Lp.

In order to detect the presence of Lp in a sample, the aptamers of the present disclosure are admixed with the sample under conditions allowing the formation of a complex between the aptamers and Lp. In such conditions, the presence of complex between the aptamer and Lp is indicative of the presence of Lp in the sample. Still in such conditions, the absence of a complex between the aptamer and Lp is indicative of the absence of Lp in the sample. In such method, it is possible to quantify the amount of the Lp in the sample, especially when the aptamer is modified to be associated with a detectable label (e.g., a radioactive label, an enzymatic label or a fluorescent label for example). By measuring the signal associated with the label, it is possible to determine or estimate the amount complexes formed between the aptamer and Lp. Alternatively, the aptamer is associated (covalently or non-covalently) to the surface of a solid support or of a sensor and the presence of the complex is measured at the surface of the solid support or the sensor. In some embodiments, the method is performed at room temperatures (e.g., between 20 and 30° C.) and the detection of the complex between the aptamers of the present disclosure and Lp is observed in real time (e.g., less than 60, 50, 40, 30, 20, 10, 9, 8, 7, 6, 5, 4, 3, 2 or 1 minute). In some embodiments, the sample is resuspended or diluted in an aqueous solution, water or an artificial fresh water medium.

In embodiments in which the aptamer is associated with a chromogenic or colorimetric label, the method can include a step of performing colorimetry (e.g., microscopy, test strip assay) for determining the presence of the complex. In embodiments in which the aptamer is associated with a fluorescent label, the method can include a step of performing a fluorescent-based assay (such as microscopy and/or flow cytometry) for determining the presence of the complex. In embodiments in which the aptamer is associated with a radioactive label, the method can include a step of performing a radioactive-based assay for determining the presence of the complex.

In some embodiments, the aptamer is affixed to a surface and may or may not be labelled. For example, in one embodiment, the aptamer (which is not labelled) can be affixed to the surface of a sensor (such as a sensor chip) which is designed to capture modifications (such as optical modifications) upon the formation of the complex (e.g., surface plasmon resonance). In another embodiment, the aptamer (which can be labelled) can be affixed to the surface of a solid support (e.g., a well, a test strip or a dip stick) and be designed to capture modifications (such as the formation of a signal) upon the formation of the complex. In another embodiment, at least two aptamers are used, one is affixed to a support and another one is provided in a soluble state with a detectable signal (such as quantum dots). In such embodiment, in the presence of Lp, Lp would bind to both the affixed aptamer and the soluble aptamer, thereby bringing the soluble aptamer (and its associated signal) closer to the surface of the support. Determining the signal associated with the support could be used to detect the presence of Lp in the sample.

In some embodiments, the method can also include a washing step so as to remove aptamers that have not formed a mixture with Lp or have formed a non-specific mixture with other components of the sample. The washing step can remove the aptamers from the sample or dissociate them from the other components of the sample. When the aptamers are presented on a solid support or on a sensor, the washing step can remove components which have non-specifically associated with the aptamers.

In some embodiments, the sample is provided as a water sample or resuspended in water or an artificial water medium prior to contacting the aptamer. In some additional embodiments, the sample can be modified (filtered, centrifuged, dried or diluted) prior to contacting the aptamer of the present disclosure.

In additional embodiment, the method can further comprises determining if the Lp present or suspected to be present in the sample is viable or not. Such viability determination step can include, for example, performing a live/dead assay using a specific dye and performing, for example, microscopy or flow cytometry. This viability determination step can be taken under consideration to determine if the Lp present in the complex is viable or not.

In some further embodiments, the method can further comprises identifying Lp cells from the cells being present in the sample. This can be done by visualizing the cells of the sample and labelling Lp cells with the aptamers of the present disclosure.

In another embodiment, the Lp-specific aptamers can be used in an imaging method to detect the presence and localize Lp in a subject or a water system. In such embodiment, the aptamers of the present disclosure (preferably modified to be associated with a detectable label) are administered to the subject under conditions or added to a water system to allow the formation of a complex between the aptamers and Lp. The subject or the water system is then submitted to an imaging technique to determine if the detectable label associated with the aptamers localize in one or more areas in the subject or of the water system. The detection of the label in the subject or the water system is indicative of the presence (and optionally the localization) of one or more Lp cells in the subject.

In yet another embodiment, the Lp-specific aptamers can be used to enrich or purify Lp from a sample comprising other components than Lp. In such embodiments, the Lp-specific aptamers are modified either to bear or be associated with an affinity label or the surface of a support (a bead, a column, or a microfluidic device for example). The Lp-specific aptamers are admixed with the sample (which is preferably a liquid sample, such as, for example, a water sample) under conditions allowing for the formation of a complex between the Lp-specific aptamers and Lp. Then, when the aptamer is associated with an affinity label, the complex can be retrieved from the sample using the affinity label present on or associated with the aptamers in order to enrich the concentration or even purify Lp from the sample. Alternatively, when the aptamer is associated with a solid support, the solid support is washed from the unbound elements of the sample to enrich or purify Lp.

In another embodiment, the present disclosure provides a method of using the aptamers, the aptamer variants or the aptamer fragments described herein as "leads" to screen for aptamers having improved properties. As such, the present disclosure also provides a method of determining if an aptamer (herein referred to as a test aptamer) would be useful for the specifically binding to Lp. In some embodiments, the method can be used to screen a library of aptamers having at least one nucleotide substitution, addition or deletion when compared to the aptamers/variants/fragments of the present disclosure. In order to do so, the test aptamer is contacted with Lp to obtain a test level of affinity towards Lp. In some embodiments, the test aptamer can also be contacted with other *Legionella* species or other bacterial species (such as *Pseudomonas* sp., *Brevundiomonas* sp., *Bacillus* sp., *Staphlyococcus* sp. *Sphingomonas* sp., *Stenotrophomonas* sp. and/or *Cupriavidus* sp.) to obtain a test level of specification towards Lp. The contacting step between the test aptamer and Lp and other bacterial species can be done in vivo or in vitro. Once the test level has been determined it is compared to a control level of the biological activity of Lp. The control level can be derived from or obtained by contacting Lp with the aptamer described herein (such as, for example R10C5 and/or R10C1), the aptamer variant described herein or the aptamer fragment described herein. Optionally, the method can comprise determining the control level of the biological activity of Lp and providing the aptamer, the aptamer variant or the aptamer fragment. Once the comparison is made, then it can be determined if the test aptamer is useful for specifically binding and detecting Lp. If the test level is equal to or higher to the control level (e.g., if the test aptamer binds with more affinity or specificity to Lp than the control aptamers, the aptamer variants or the aptamer fragments), then it is determined that the test aptamer is useful for specifically binding to Lp. However, if the test level is lower than the control level (e.g., if the test aptamer binds with less affinity or specificity towards Lp than the control aptamers, the aptamer variants or the aptamer fragments), then it is determined that the test aptamer is not useful for specifically binding to Lp.

Example

Bacterial Strains and Culture Conditions.

The environmental Lp strain lp120292, isolated from a cooling tower implicated in the 2012 outbreak in Quebec City, was used as the target strain for aptamer generation (Lévesque et al. 2016). The strain Lp*GFP is lp120292 transformed with plasmid pXDC31 expressing the green fluorescent protein (GFP) under the Ptac promoter (Hovel-Miner et al. 2009). The thymidine auxotroph Lp strain Lp02, derived from Lp Philadelphia-1 was used to confirm binding of the aptamers (Berger and Isberg 1993). Lp was cultured on CYE (ACES-buffered charcoal yeast extract) agar plates supplemented with 0.25 mg/ml L-cysteine and 0.4 mg/ml ferric pyrophosphate, at 37° C. for 3 days. Lp*GFP strain was grown on CYE media supplemented with 5 μg/ml chloramphenicol and 1 mM isopropyl β-D-1-thiogalactopyranoside. For liquid culture, Lp was suspended in AYE (ACES-buffered yeast extract) broth supplemented with 0.25 mg/ml L-cysteine and 0.4 mg/ml ferric pyrophosphate until post-exponential phase ($OD_{600}$ of 2.0). *Pseudomonas putida* KT2440 and *Pseudomonas fluorescens* LMG1794, were first cultured on LB agar plates at 30° C. for 24 hours and then grown in LB medium (Difco) until the cultures reached post-exponential phase ($OD_{600}$ of 2.0-2.5). *Pseudomonas* sp., *Brevundiomonas* sp., *Bacillus* sp., *Staphlyococcus* sp. *Sphingomonas* sp., *Stenotrophomonas* sp. and *Cupriavidus* sp. were isolated from cooling towers. Briefly, the bacteria were isolated on nutrient agar incubated at 30° C. for 24 h. Isolates were then classified using 16S rDNA sequencing. These strains were first cultured on nutrient agar plates (Difco) at 30° C. for 24 hours and then grown in nutrient broth medium (Difco) overnight until the cultures reached post-exponential phase ($OD_{600}$ of 2.0-2.5).

Oligonucleotides Library and Primers.

A random ssDNA library of $10^{15}$ sequences was chemically synthesized and purified by HPLC (Integrated DNA Technologies). The library consisted of a central random region of 45 nucleotides flanked by two different primer binding regions at the 5' and 3' ends: 5'-GCAATGGTACGGTACTTCC-45N-CAAAAGTGCACGCTACTTTGCTAA-3' (SEQ ID NO: 3). The forward and reverse primers were conjugated with fluorescein (FITC) and biotin, respectively. The forward primer (FP) sequence is 5'-fluorescein-GCAATGGTACGGTACTTCC-3' (SEQ ID NO: 4). The reverse primer (RP) sequence is 5'-biotin-TTAGCAAAGTAGCGTGCACTTTTG-3' (SEQ ID NO: 5). FITC was used to quantify ssDNA and monitor the SELEX procedure via flow cytometry. The biotin was used in conjunction with streptavidin coated magnetic beads (Promega) to generate ssDNA from the amplified double-stranded aptamer pool following PCR. For cloning and sequencing, PCR was performed with unmodified versions of the primers.

Bacterial Cell-SELEX Procedure.

Figure 1:
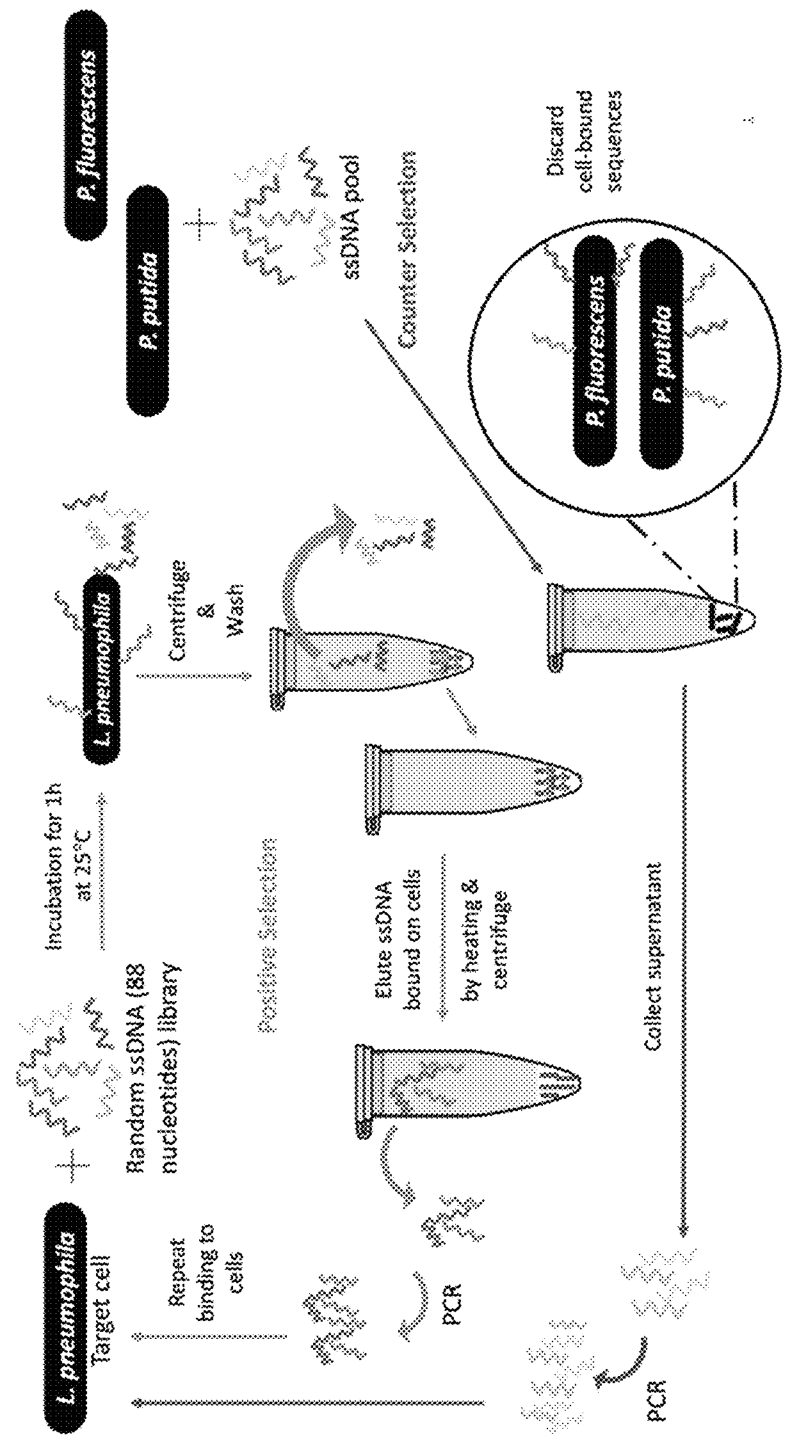
FIG. 1 provides a schematic illustration of bacterial cell-SELEX procedure used in the example. A random library of oligonucleotides is incubated with Lp lp120292 at room temperature for 1 h. Sequences that do not bind are washed off and the cell-bound sequences are then released and amplified via PCR. The resulting sequences are then submitted to another round of positive selection. *P. fluorescens* and *P. putida* were used to perform counter-selection rounds to eliminate non Lp specific sequences.

Cell-SELEX was performed as previously described (Kim et al. 2013). Each round of SELEX consisted of three steps: Binding and elution, amplification, and recovery of ssDNA. Ten rounds of positive selection and two rounds of counter selection were performed (FIG. 1). The first round of counter selection was performed with *P. putida* KT2440; the second one with *P. fluorescens* LMG1794.

Binding and Elution:

Cell-SELEX was performed with cells suspended in an artificial freshwater medium (Fraquil) to replicate the physiological state of nutrient-limited environmental conditions (Li, Mendis et al. 2015, Mendis, McBride et al. 2015). Fraquil was prepared as described previously (Morel, Westall et al. 1975) with a final iron concentration of 10 nM and filter-sterilized using a 0.2 urn filter (Sarstedt). Post-exponential phase cultures were rinsed twice with Fraquil (6000 g, 15 minutes) and suspended in Fraquil at an $OD_{600}$ of 1 corresponding to a concentration of $10^9$ CFU/ml. The concentration of cells was confirmed by CFU counts for each round. The suspension was incubated at room temperature for 24 h. Fraquil exposed cells were washed three times in 1× binding buffer (phosphate buffered saline with 0.1 mg/ml salmon sperm DNA, 1% bovine serum albumin, and 0.05% Tween 20) at room temperature (25° C.) using 6,000 g for ten minutes. The cell pellets were then suspended in 330 μl of 1× binding buffer. The aptamer pool was denatured by heating at 95° C. for 10 minutes, cooled immediately on ice for 10 minutes, and added to the cell suspension. Finally, 1× binding buffer was added to a total volume of 1 ml. For the first round, 32 μg of the initial library was used. For the subsequent rounds, approximately 400 ng of aptamer pool was used. The final mixture was incubated at 25° C. for 1 hour with mild shaking using a tube rotator at 150 rpm. Following incubation, the mixture was centrifuged at 6000 g for 10 minutes and washed twice with wash buffer (phosphate buffered saline containing 0.05% Tween 20) to remove unbound sequences. To elute the bound sequences from the cells, the final cell pellet was resuspended in 100 μl nuclease free water (Ambion) and heated at 95° C. for 10 minutes and immediately placed on ice for 10 minutes. After centrifuging at 6,000 g for 10 minutes at 25° C., the supernatant was collected and purified using overnight ethanol precipitation at −20° C. with 5 μg of glycogen as a carrier to recover the eluted ssDNA. The pellet was recovered, dried and suspended in nuclease free water (Ambion). The concentration and quality of the ssDNA was determined using a Nanodrop spectrophotometer (Thermofisher). For counter-selection the supernatant containing the unbound sequences was collected and purified via ethanol precipitation, as described above. To ensure there was no amplification or collection of unwanted bacterial DNA (instead of the desired amplification and collection of ssDNA oligonucleotides), a control sample consisting of bacterial cells without aptamer was included in each round.

PCR Amplification.

The purified aptamer pool was then amplified by PCR with One Taq DNA polymerase (NEB), according to the manufacturer's protocol. All primers were used at a final concentration of 0.5 μM. PCR conditions were as follows: initial heat activation at 95° C. for 5 min and 25 cycles of 95° C. for 30 s, 56.3° C. for 30 s, 72° C. for 10 s, and a final extension step of 10 min at 72° C. After amplification, the concentration and size of the PCR product were confirmed by gel electrophoresis using a 2.0% agarose gel. PCR products were then purified using a MinElute PCR Purification Kit (Qiagen). As expected, no amplification was observed for the control samples, lacking aptamer template.

Recovery of ssDNA.

Streptavidin coated magnetic beads (Promega Technology) were used, according to the manufacturer's recommendation. Briefly, 600 μg of magnetic beads were washed twice and then resuspended in 900 μl of washing buffer (phosphate buffered saline with 0.05% Tween 20). Next, approximately 1 μg of PCR product was incubated with the magnetic beads for 10 min, mixing gently by inversion after every few minutes. The mixture was then washed in 1 ml of washing buffer. Finally, the beads were incubated with 500 μl of 200 mM NaOH for 5 minutes. The supernatant was then collected, and the FITC-labelled ssDNA was purified using ethanol precipitation as mentioned previously and quantified with a Nanodrop spectrophotometer (Thermofisher).

Monitoring of SELEX by Flow Cytometry.

The binding of the FITC-labelled aptamer pools from rounds 1 (R1), 6 (R6), 7 (R7), 8 (R8) and 10 (R10) to Lp was assessed using flow cytometry. Briefly, 35 nM of aptamer pools from each of these rounds was incubated with $10^6$ CFU/ml of Lp cells at 25° C. for 1 hour. Analysis was performed on a Guava easyCyte (Millipore) using the green fluorescence channel. A total of 5,000 events were recorded. Unlabeled cells were used as a control to measure autofluorescence. The Lp*GFP strain, producing strong green fluorescence from GFP, was used to adjust the gain of the green fluorescence channel. For analysis, a gate was first defined based on the forward and side scatters that included most of the cells. Then, a histogram of the number of cells vs the fluorescence intensity was used to define a region named Green_Lp where cells were considered positive for green fluorescence and therefore stained with aptamers. This region was setup to include very few cells of the unstained control and therefore represent fluorescence above the auto-fluorescence. Aptamer pools from R10 alone, without cells, was also analyzed to ensure that the aptamer alone was not forming aggregates that would be confused with cells.

Cloning and Sequencing.

To identify sequences binding to Lp, the aptamer pool from the $10^{th}$ round of SELEX was cloned with the pGEMT-easy Cloning and Ligation Kit (Promega). To investigate the effect of counter-selection on the aptamer pools, the aptamers from the $6^{th}$ round of SELEX were also cloned and sequenced. Positive colonies, containing aptamer inserts, were determined via blue-white screening and confirmed by PCR. Plasmids were extracted and purified using a Miniprep Kit (Qiagen) and sequenced by Sanger Sequencing at the Plate-forme d'Analyse Génomique of Laval University. Secondary structures of the aptamer sequences were determined using the mfold web server using default parameters (Zuker 2003).

Characterization of Aptamers R10C5 and R10C1.

The binding of the aptamers R10C5 and R10C1 to Lp and to the species used for counter-selection was characterize further. R10C5 and R10C1 were individually synthesized with FITC at the 5' end (Integrated DNA Technology).

Determination of the Disassociation constant ($K_D$): To determine the $K_D$ of R10C5 and R10C1, varying concentrations of FITC-tagged aptamers (1000 nM, 100 nM, 10 nM, and 1 nM) were incubated with $10^6$ CFU/ml of Lp cells suspended in Fraquil and the fluorescence obtained at each concentration was measured using flow cytometry, as described above, in triplicate. The number of bound cells (FITC-positive) were recorded and used to determine the $K_D$ by interpolating the logarithmic curve using the GraphPad Prism 7.03 software.

Specificity assay: To determine the specificity of R10C5 and R10C1 for Lp cells, the binding to *Pseudomonas* strain was tested using flow cytometry. All cells were suspended in Fraquil and prepared as described above for cell-SELEX. Briefly, 100 nM of R10C5 and R10C1 was incubated with $10^7$ CFU/ml of the strain used for SELEX (lp120292), another Lp strain (Lp02), and the strains used for counter-selection (*P. putida* KT2440 and *P. fluorescens* LMG1794) and environmental isolates from cooling towers (*Pseudomonas* sp., *Brevundiomonas* sp., *Bacillus* sp., *Staphylococcus* sp., *Sphingomonas* sp., *Stenotrophomonas* sp. and *Cupriavidus* sp.) for 1 hour at 25° C. with mild shaking. lp120292 was also incubated with 100 nM of a FITC-labeled scrambled sequence of aptamer R10C5 (5'-fluorescein-ACAGAATCAGTTCGAGTACATACGCGCG AAGACTCCTAAGGCCGTAGCGTTCTTCCCGGTAAT ACCATG, SEQ ID NO: 18) and R10C1 (5'-fluorescein-TGTACTCCCGCGTCCCACCTGC-TACCCGAAATAGAGTTTCCCTAGAAAGG CTTGCC-CAAC, SEQ ID NO: 19). The suspension was centrifuged for 10 minutes at 6000 g to eliminate excess aptamer and resuspended in Fraquil. These suspensions were then analyzed using flow cytometry as described above. This experiment was done in triplicate. Cells suspended in Fraquil without any aptamer added were used as controls. The percentage of bound cells was determined as described above. Statistical differences were assessed using a one-way ANOVA and Dunnett correction for multiple comparison using Graphpad prism 7.03.

Fluorescence Microscopy Assay.

FITC-labelled R10C5 and R10C1 aptamer (500 nM) were incubated with $10^6$ CFU/ml of target cell lp120292 or counter-selection strain LMG1794 for 1 hour at 25° C. on a tube rotator at 150 rpm. Cells were suspended in Fraquil as mentioned previously. Negative controls included cells suspended in Fraquil without any aptamer and aptamer suspended in Fraquil, without cells added. The suspensions (10 μl) were dropped on a glass slide (Fisherbrand), and a #1.5 cover slip (Fisherbrand) was used to make a thin layer. Using a 63× oil immersion objective, brightfield and fluorescent images of bacteria were observed using an Apotome epifluorescence microscope (Zeiss) using pre-set excitation and emission filters for FITC, 495 nm and 519 nm respectively.

Selection of Aptamers Binding to Lp.

Cell-SELEX was used to select aptamers binding specifically to lp120292. This strain was selected because it was involved in the Quebec City Outbreak in 2012 (Lévesque, Lalancette et al. 2016). To mimic the physiological state of Lp in water system, Lp cells were grown to post-exponential phase and suspended in Fraquil for 24 h at 25° C. to induce starvation and the associated morphological and physiological changes (Li, Mendis et al. 2015, Mendis, McBride et al. 2015).

Several rounds of SELEX were performed and did not yield any results (data not shown). The SELEX conditions were modified (as indicated above) and seven rounds of positive selection were performed, followed by one round of counter-selection, two rounds of positive selection, an additional round of counter-selection and a final round of positive selection (FIG. 1). Two *Pseudomonas* strains were used for counter-selection because they are also Gram-negative proteobacteria frequently isolated from water systems where Lp is found.

Figure 2:
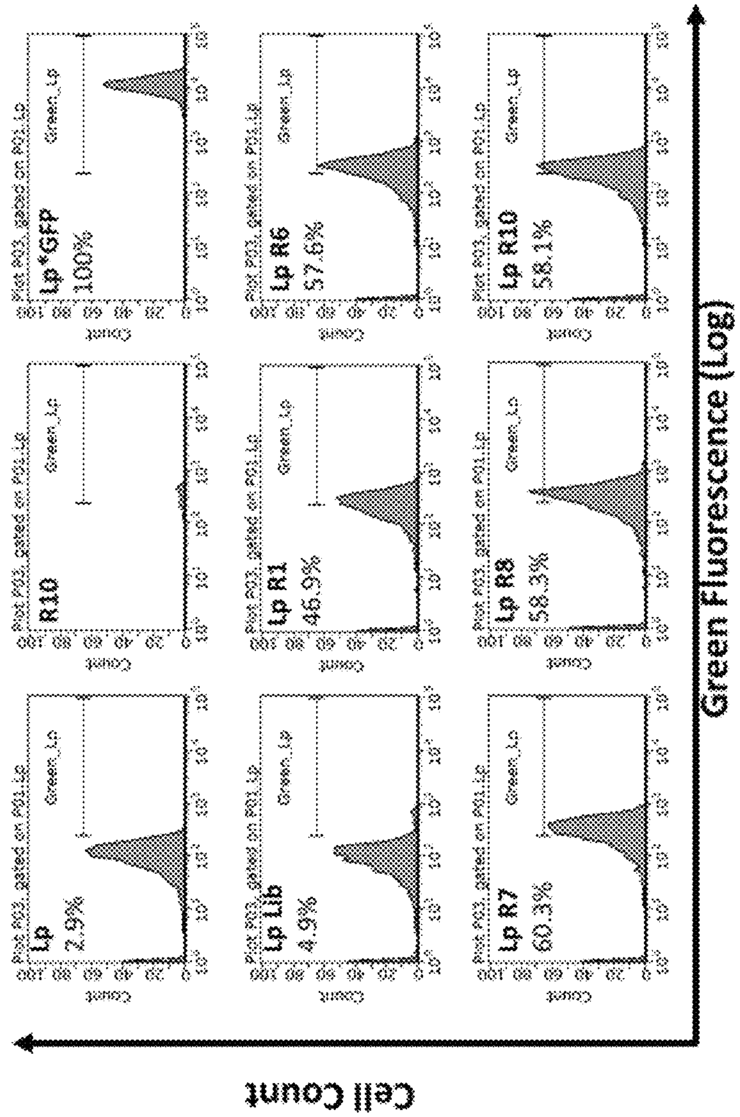
FIG. 2 shows the fluorescent labeling of Lp with aptamers pools obtained after selected round of SELEX. Lp strain lp120292 was incubated without aptamers (Lp), with 35 nM of the aptamer library (Lp-lib) and of the aptamer pools obtained after round 1 (Lp-R1), 6 (Lp-R6), 7 (Lp-R7), 8 (Lp-R8) and round 10 (Lp-R10). The fluorescence obtained with aptamer from round 10 alone (R10), without cells, was also evaluated. Lp*GFP is a GFP producing version of lp120292 and is used as a positive control. The percentages refer to the proportion of cells with fluorescence above the autofluorescence, falling in the Green_Lp region.

To monitor the progress of the SELEX procedure and ensure that the proportion of sequences binding to Lp was increasing, the binding of the FITC-labelled aptamer pools from rounds 1 (R1), 6 (R6), 7 (R7), 8 (R8) and 10 (R10) to Lp was examined using flow cytometry. Cells incubated with the initial aptamer library showed minimal fluorescence compared to the negative controls (FIG. 2, Lp Lib). Cells incubated with aptamer from the first positive selection round showed a drastic increase in fluorescence (FIG. 2, Lp R1). The saturation in the fluorescence intensity and the percentage of bound cells starting at R6 suggests that the pool is dominated by sequences binding to Lp (FIG. 2, R6, R7, R8, R10). A small decrease in fluorescence and percentage of bound cells at R8 suggests that the first counter-selection step removed a few sequences. The fluorescence intensity remains similar between round 8 and 10 indicating that the second round of counter-selection did not remove Lp-specific sequences and that the strategy was successful in retrieving aptamers binding to Lp.

Cloning and Sequencing.

Analyzing the sequences obtained from the $10^{th}$ round of positive selection allowed for identifying two different ssDNA aptamers, named R10C5 and R10C1 (Table 1 and FIG. 3). Of the 13 sequences that were retrieved, 12 of them were R10C5 whereas 1 was R10C1. In contrast, the survey of a non-exhaustive list of the sequences present in the R6 aptamer pool revealed eight different sequences out of 9 clones, but none similar to R10C1 and R10C5. This illustrates the directional evolution of the pool as a result of the additional positive selection rounds and counter-selection steps (Schutze, Wilhelm et al. 2011, Stoltenburg and Strehlitz 2018). A strong bottleneck effect was likely caused by the last four positive selection rounds and the apparently stringent counter-selection rounds, which most likely led to the removal of several aptamers.

TABLE 1

Aptamer's sequences from round 6 and round 10.

| APTAMER ID | SEQUENCE (SEQ ID NO:) | FREQUENCY(%) |
|---|---|---|
| | Pre Counter-SELEX (Round 6) | |
| R6C1 | GCAATGGTACGGTACTTCCCCACT AACGCGCCCACGCACCCCTCGGCT ACATCCAGCACCCGCCCAAAAGTG CACGCTACTTTGCTAA (SEQ ID NO: 6) | 2/9 (22.2%) |
| R6C3 | GCAATGGTACGGTACTTCCCCACT CCACGCATCACAGCCTTTCACTGC CCACGCCTCAAAAGTGCACGCTAC TTTGCTAA (SEQ ID NO: 7) | 1/9 (11.1%) |
| R6C7 | GCAATGGTACGGTACTTCCACCAC CGGAGTGTGCTTCAGCCGTGGTAC AATACTGCCGTGTATCCAAAAGTG CACGCTACTTTGCTAA (SEQ ID NO: 8) | 1/9 (11.1%) |
| R6C11 | GCAATGGTACGGTACTTCCCCCAC TGCACACACAAAGGGCCAGCATCA ACACACGCGCCGTTCCAAAAGTGC ACGCTACTTTGCTAA (SEQ ID NO: 9) | 1/9 (11.1%) |
| R6C12 | GCAATGGTACGGTACTTCCCACCC CGCCACGCCGATAGCCTCCCATAC TCCCCCCGCANGTCCA AAAGTGC ACGCTACTTTGCTAA (SEQ ID NO: 10) | 1/9 (11.1%) |
| R6C15 | GCAATGGTACGGTACTTCCCGCGC ACCCCACACCTCCGCACACCGCAT GCCTCCCCTTAGGCCCCAAAAGTG CACGCTACTTTGCTAA (SEQ ID NO: 11) | 1/9 (11.1%) |
| R6C16 | GCAATGGTACGGTACTTCCCACTG CCGAACGCGCCCTCTCCTGCTGCC TCCACACATGGTCGCCAAAAGTGC ACGCTACTTTGCTAA (SEQ ID NO: 12) | 1/9 (11.1%) |
| R6C18 | GCAATGGTACGGTACTTCCCCCAC CAAGCCCATACACGTACAGCCTAC CACAATCCACATCGGGCCAAAAGT GCACGCTACTTTGCTAA (SEQ ID NO: 13) | 1/9 (11.1%) |
| | Post Counter-SELEX (Round 10) | |
| R10C5 | GCAATGGTACGGTACTTCCGGACA GTGCTGAAAACTGTGACCCCCCAA AAGTGCACGCTACTTTGCTAA (SEQ ID NO: 14) | 12/13(92.3%) |
| R10C1 | GCAATGGTACGGTACTTCCCCACC CCACGCTGCTCCCAAAAGTGCACG CTACTTTGCTAA (SEQ ID NO: 15) | 1/13 (7.7%) |

Determination of $K_D$.

Figure 4A:
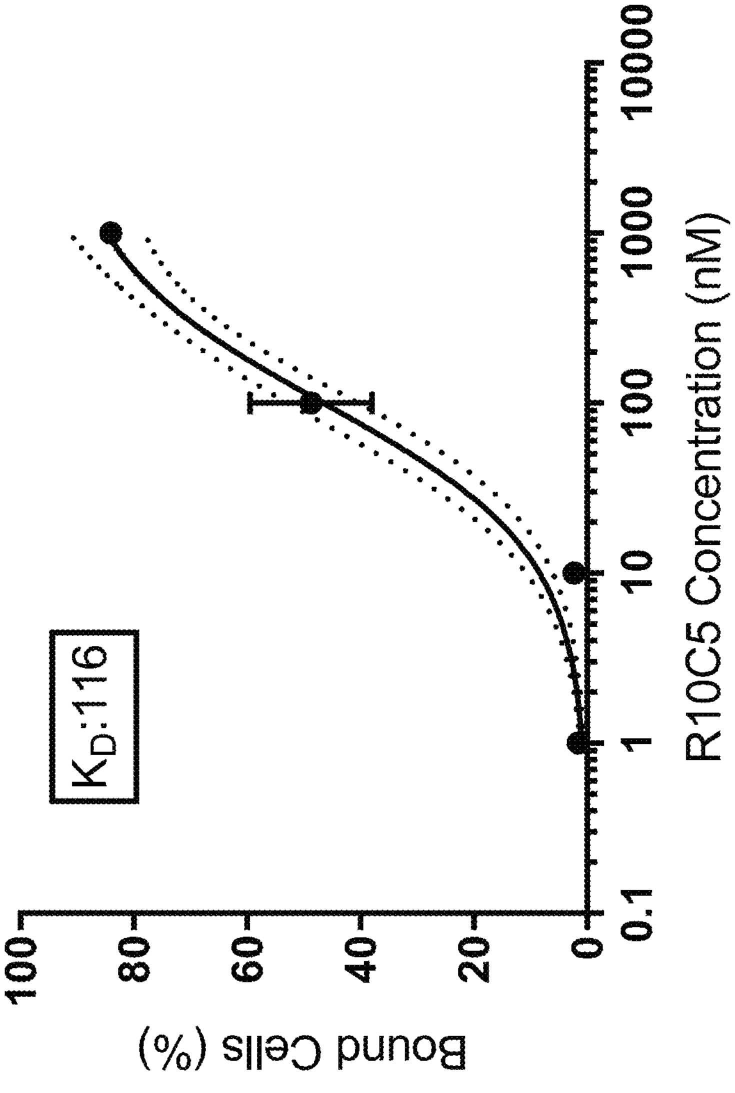
FIG. 4A provides the determination of the $K_D$ of the aptamer R10C5. Lp (lp120292) was incubated with 10-fold dilutions of the FITC-tagged aptamers and the fluorescence was measured by flow cytometry. The number of cells displaying fluorescence above the autofluorescence were counted as bound cells, as described in FIG. 2. The graphs show the average and standard deviation of three experiments. The equilibrium dissociation constant, $K_D$ was calculated using the GraphPad Prism 7.03 software.
Figure 4B:
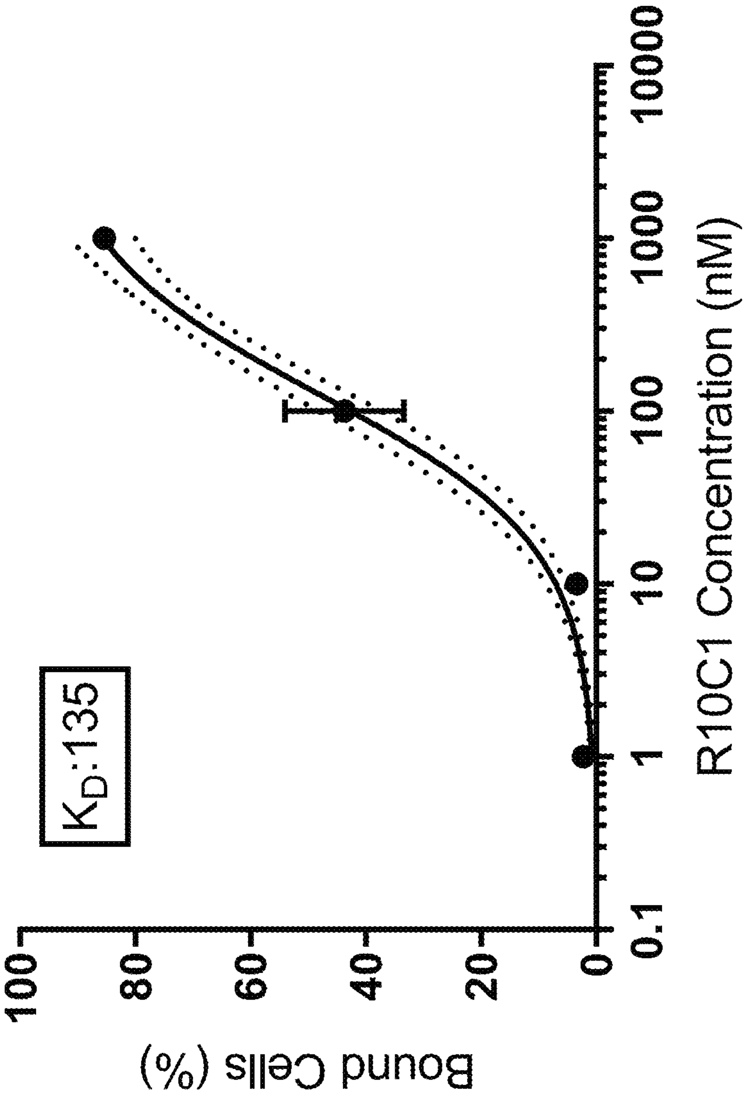
FIG. 4B provides the determination of the $K_D$ of the aptamer R10C1. Lp (lp120292) was incubated with 10-fold dilutions of the FITC-tagged aptamers and the fluorescence was measured by flow cytometry. The number of cells displaying fluorescence above the autofluorescence were counted as bound cells, as described in FIG. 2. The graphs show the average and standard deviation of three experiments. The equilibrium dissociation constant, $K_D$ was calculated using the GraphPad Prism 7.03 software.

The calculated $K_D$ is 116 nM for R10C5 and 135 nM for R10C1 (FIG. 4). These values are comparable to high affinity antibodies that typically show nanomolar ranges of $K_D$ for small protein targets (Zhou and Rossi 2017). These values are also consistent with published aptamers created against whole bacterial pathogens. For example, aptamers isolated against *Escherichia coli, Enterobacter aerogenes, Klebsiella pneumoniae, Citrobacter freundii, Bacillus subtilis*, and *Staphylococcus epidermidis* showed $K_D$ ranging from 9.22-38.5 nM (Song, Sekhon et al. 2017). Two 62 nt aptamers binding to *Staphylococcus aureus* have $K_D$ of 35 nM and 129 nM (Chang, Yang et al. 2013).

Specificity of R10C5 and R10C1.

Figure 5A:
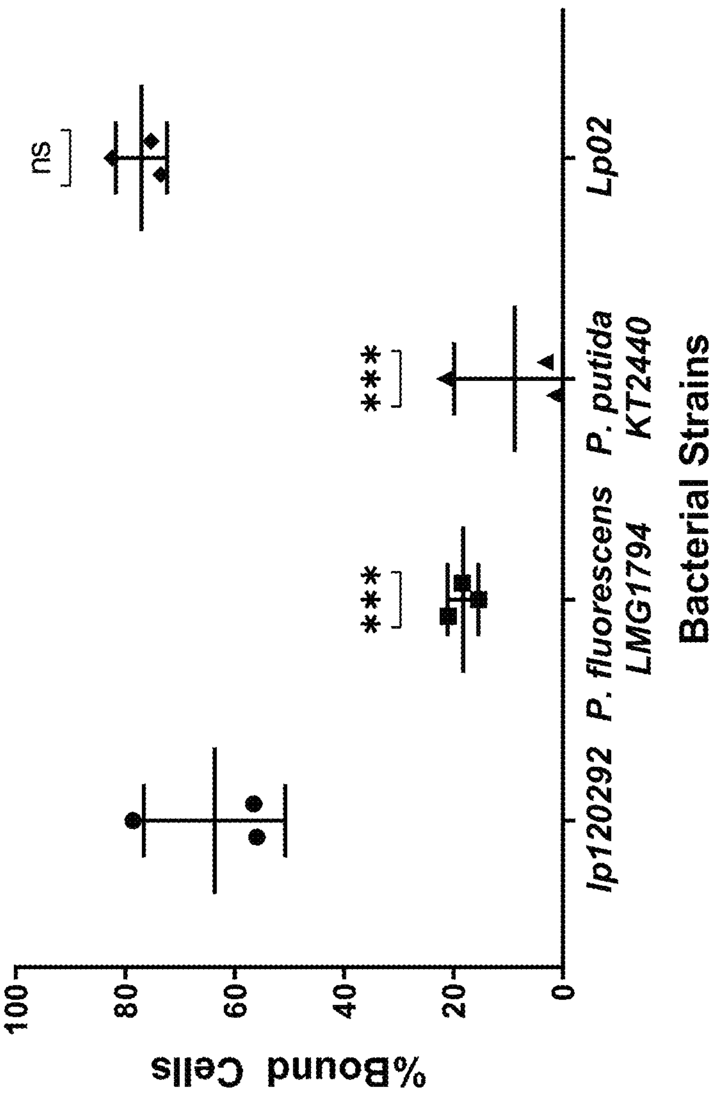
FIG. 5A provides the specificity of the R10C5 aptamer binding to Lp strains lp120292 (positive control), to *Pseudomonas* strains as well as the binding of R10C5 to Lp strain Lp02 as analyzed by flow cytometry. It provides the percentage of bound cells to the R10C5 aptamer. The values of three experiments are shown with the mean and standard deviation. A one-way ANOVA with a Dunnett correction for multiple comparisons was used to infer statistical significance compared to lp120292: * $P<0.05$,  $P<0.01$, * $P<0.001$, **** $P<0.0001$.
Figure 5B:
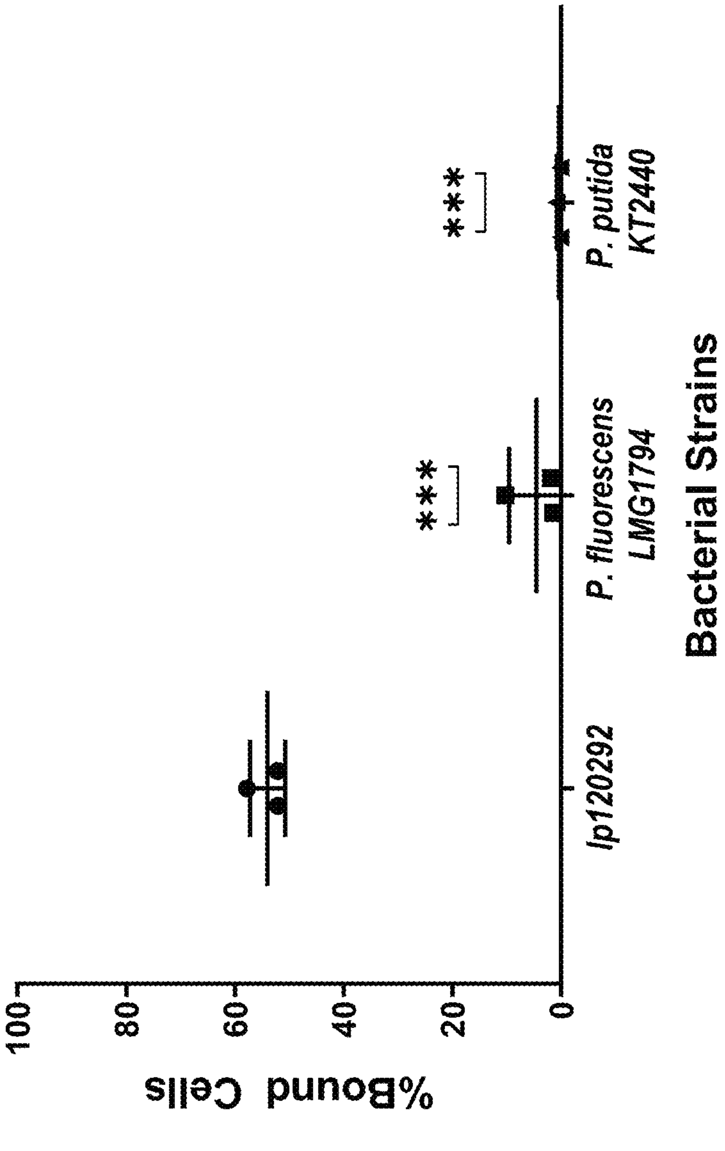
FIG. 5B provides the specificity of the R10C1 aptamer binding to Lp strains lp120292 (positive control), to *Pseudomonas* strains as well as the binding of R10C5 to Lp strain Lp02 as analyzed by flow cytometry. It provides the percentage of bound cells to the R10C1 aptamer. The values of three experiments are shown with the mean and standard deviation. A one-way ANOVA with a Dunnett correction for multiple comparisons was used to infer statistical significance compared to lp120292: * $P<0.05$,  $P<0.01$, * $P<0.001$, **** $P<0.0001$.
Figure 5C:
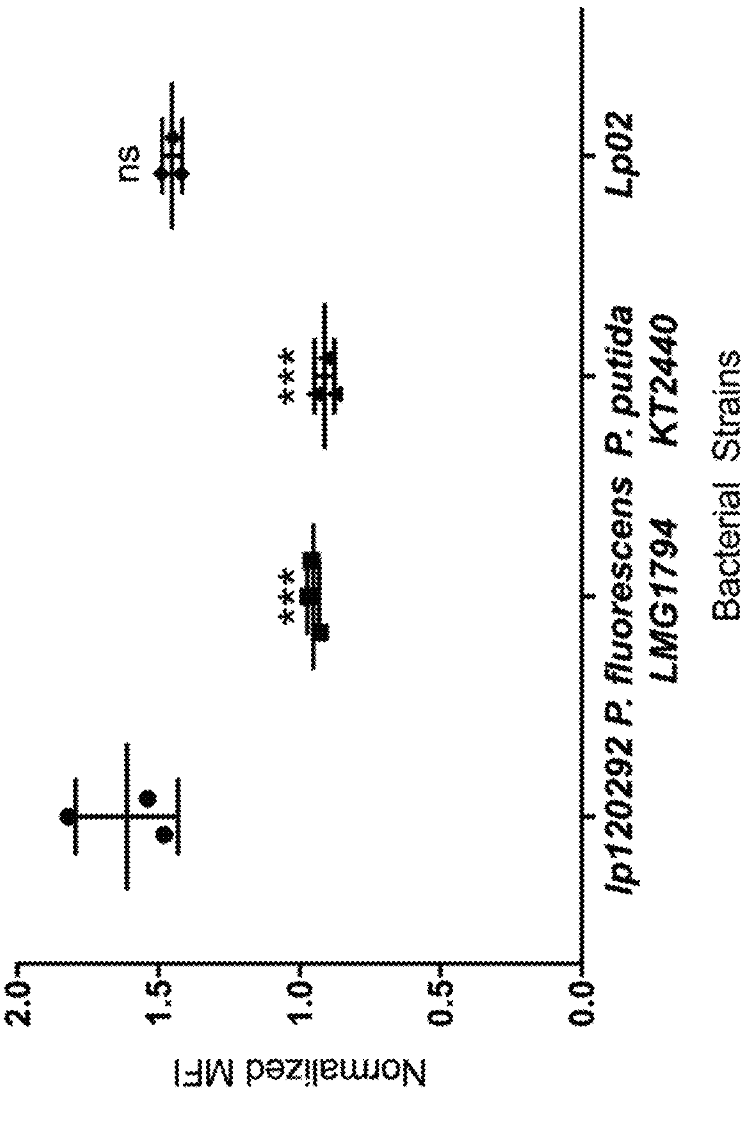
FIG. 5C provides the specificity of the R10C5 aptamer binding to Lp strains lp120292 (positive control), to *Pseudomonas* strains as well as the binding of R10C5 to Lp strain Lp02 as analyzed by flow cytometry. It provides the normalized median fluorescence intensity of the R10C5 aptamer. The values of three experiments are shown with the mean and standard deviation. A one-way ANOVA with a Dunnett correction for multiple comparisons was used to infer statistical significance compared to lp120292: * $P<0.05$,  $P<0.01$, * $P<0.001$, **** $P<0.0001$.
Figure 5D:
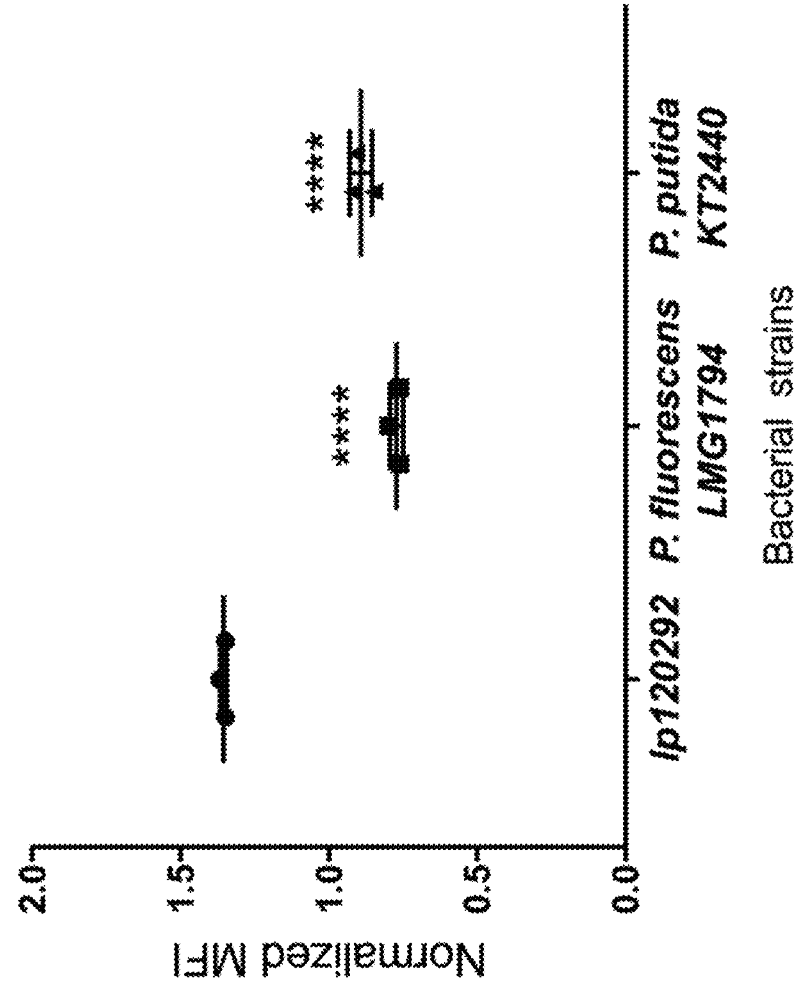
FIG. 5D provides the specificity of the R10C1 aptamer binding to Lp strains lp120292 (positive control), to *Pseudomonas* strains as well as the binding of R10C5 to Lp strain Lp02 as analyzed by flow cytometry. It provides the normalized median fluorescence intensity of the R10C1 aptamer. The values of three experiments are shown with the mean and standard deviation. A one-way ANOVA with a Dunnett correction for multiple comparisons was used to infer statistical significance compared to lp120292: * $P<0.05$, $P<0.01$, * $P<0.001$, **** $P<0.0001$.
Figure 6:
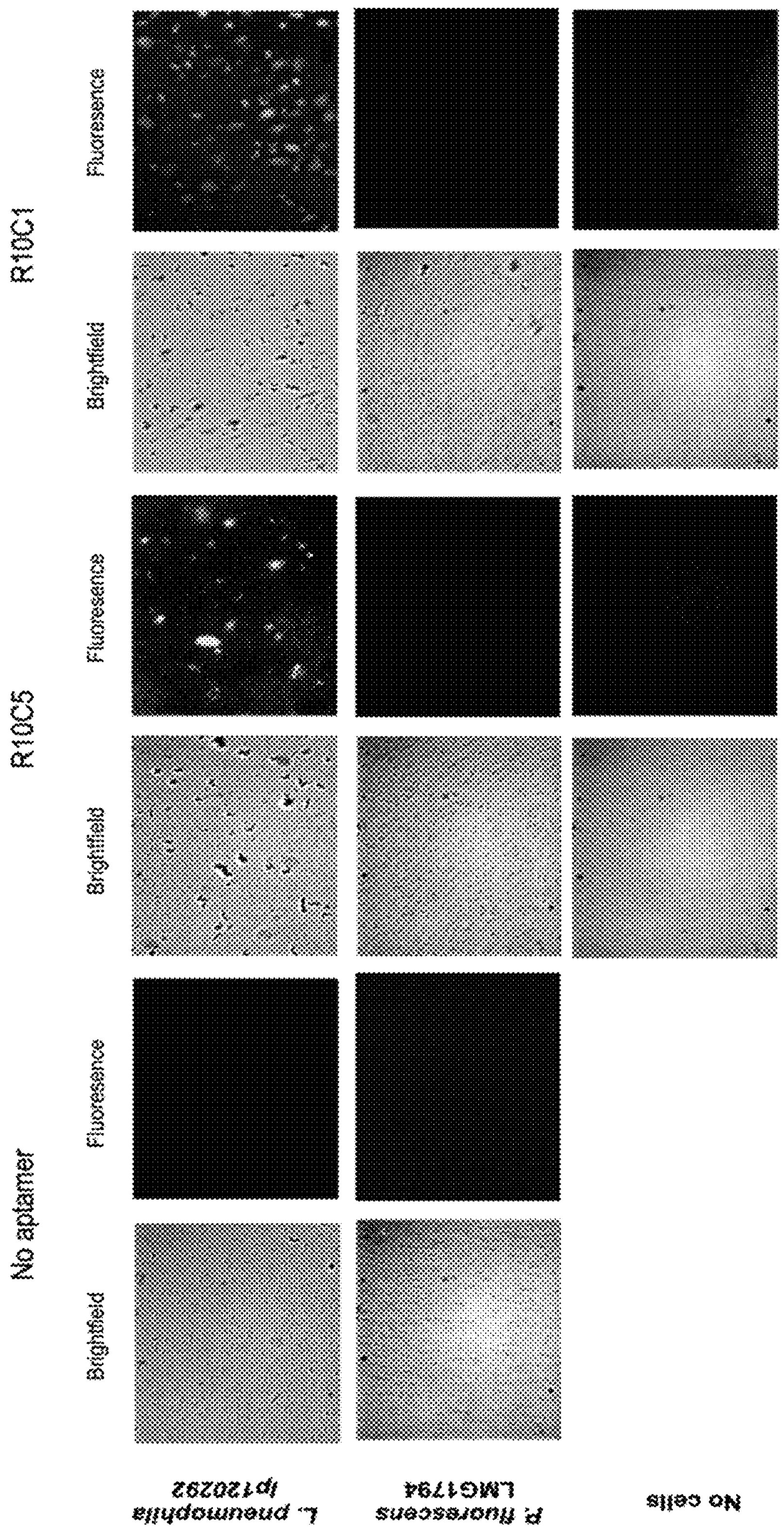
FIG. 6 provides the specificity of R10C5 and R10C1 aptamer by measuring their ability to bind to *P. fluorescens*

The binding of R10C5 and R10C1 to the strains used for counter-selection was then evaluated. FIGS. 5A and 7A shows that around 60% of lp120292 cells are stained by R10C5, consistent with previous results shown in FIG. 2, but only 20% of *Pseudomonas* strains are labelled. This difference was highly significant. R10C1 also shows significantly more binding to Lp than to *Pseudomonas* (FIGS. 5B and 7B). The overall MFI of lp120292 cells labelled with R10C5 or R10C1 was significantly much higher than *Pseudomonas* strains (FIGS. 5C and D,). Note that a normalized MFI of 1 suggests that the fluorescence intensity of the cells did not increase in the presence of the FITC-tagged aptamers. The fluorescence intensity of *Pseudomonas* strains in the presence of aptamer R10C5 or R10C1 is close to 1, indicating marginal staining of *Pseudomonas* cells. The aptamer R10C5 stained Lp02 similarly to lp120292, suggesting that the binding of this aptamer is not restricted to a particular strain of Lp (FIGS. 5A and C, FIG. 7A). Moreover, both aptamers show very low binding to environmental isolates from cooling tower water. For the majority of the isolates, less than 10% of cells were labeled by the aptamers (FIGS. 7C and 7D). The specificity of these aptamers for Lp was further analyzed by fluorescence microscopy. Both aptamers strongly stained Lp (FIGS. 6 and 8) but not *P. fluorescens* LMG1794, one of the strains used for counter-selection. Overall, both aptamers are highly specific to Lp.

The cell-SELEX strategy was successful in identifying two aptamers binding to Lp with high affinity ($K_D$=116 nM for R10C5 and 135 nM for R10C1). Whereas R10C5 seems to stain Lp more strongly than R10C1, the latter seems more specific to Lp, showing minimal binding to *Pseudomonas* strain. The binding of these aptamers to other aquatic microbial species needs to be evaluated to confirm their effectiveness to detect Lp from water systems. Modification of these aptamers could be attempted to further increase their affinity for Lp and specificity. Nonetheless, these aptamers are good candidates as biorecognition elements to develop a biosensor to detect Lp in real time and in situ.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Berger, K. H. and R. R. Isberg (1993). "Two distinct defects in intracellular growth complemented by a single genetic locus in *Legionella pneumophila." Molecular Microbiology* 7(1): 7-19.

Chang, Y.-C., C.-Y. Yang, R.-L. Sun, Y.-F. Cheng, W.-C. Kao and P.-C. Yang (2013). "Rapid single cell detection of *Staphylococcus aureus* by aptamer-conjugated gold nanoparticles." *Scientific reports* 3: 1863.

Hovel-Miner, G., S. Pampou, S. P. Faucher, M. Clarke, I. Morozova, P. Morozov, J. J. Russo, H. A. Shuman and S. Kalachikov (2009). "a(S) Controls Multiple Pathways Associated with Intracellular Multiplication of *Legionella pneumophila." Journal of Bacteriology* 191(8): 2461-2473.

Kim, Yeon Seok, Min Young Song, Jongsoo Jurng, and Byoung Chan Kim. 2013. 'Isolation and characterization of DNA aptamers against *Escherichia coli* using a bacterial cell-systematic evolution of ligands by exponential enrichment approach', *Analytical biochemistry,* 436: 22-28.

Lévesque, S., C. Lalancette, K. Bernard, A. L. Pacheco, R. Dion, J. Longtin and C. Tremblay (2016). "Molecular Typing of *Legionella pneumophila* Isolates in the Province of Quebec from 2005 to 2015." *PloS one* 11(10): e0163818.

Li, L., N. Mendis, H. Trigui and S. P. Faucher (2015). "Transcriptomic changes of *Legionella pneumophila* in water." *BMC genomics* 16(1): 637.

Mendis, N., P. McBride and S. P. Faucher (2015). "Short-term and long-term survival and virulence of *Legionella pneumophila* in the defined freshwater medium Fraquil." *PloS one* 10(9): e0139277.

Morel, F. M., J. C. Westall, J. Reuter and J. P. Chaplick (1975). Description of the algal growth media 'Aquil' and 'Fraquil'. Water Quality Laboratory, Ralph Parsons Laboratory for Water Resources and Hydrodynamics, Massachusetts Institute of Technology, Technical Report 16.

Schutze, T., B. Wilhelm, N. Greiner, H. Braun, F. Peter, M. Morl, V. A. Erdmann, H. Lehrach, Z. Konthur, M. Menger, P. F. Arndt and J. Glokler (2011). "Probing the SELEX process with next-generation sequencing." *PLoS One* 6(12): e29604.

Song, M.-S., S. S. Sekhon, W.-R. Shin, H. C. Kim, J. Min, J.-Y. Ahn and Y.-H. Kim (2017). "Detecting and discriminating *Shigella sonnei* using an aptamer-based fluorescent biosensor platform." *Molecules* 22(5): 825.

Stoltenburg, R. and B. Strehlitz (2018). "Refining the Results of a Classical SELEX Experiment by Expanding the Sequence Data Set of an Aptamer Pool Selected for Protein A." *International Journal of Molecular Sciences* 19(2): 642.

Zhou, J. and J. Rossi (2017). "Aptamers as targeted therapeutics: current potential and challenges." *Nature Reviews Drug Discovery* 16: 440.

Zuker M. Mfold web server for nucleic acid folding and hybridization prediction. Nucleic Acids Res. 2003 Jul. 1; 31(13):3406-15.

What is claimed is:

1. An aptamer binding *Legionella pneumophila*, said aptamer comprising:

a nucleic acid molecule having a sequence as set forth in any one of SEQ ID Nos: 6-15.

2. The aptamer of claim 1 comprising the nucleic acid sequence of SEQ ID NO: 14.

3. The aptamer of claim 1 comprising the nucleic acid sequence of SEQ ID NO: 15.

4. The aptamer of claim 3 further comprising at least one of:

a 5' wing nucleic acid molecule covalently associated with the 5' end of the core nucleic acid molecule, wherein the 5' wing nucleic acid molecule has the nucleic acid sequence of SEQ ID NO: 1; or a 3' wing nucleic acid molecule covalently associated with the 3' end of the core nucleic acid molecule, wherein the 3' wing nucleic acid molecule has the nucleic acid sequence of SEQ ID NO: 2.

5. The aptamer of claim 1 being attached to a detectable moiety.

6. The aptamer of claim 1 being attached to a surface of a material or a sensor.

7. A solid support comprising a surface, wherein the surface is attached to the aptamer of claim 1.

8. A sensor comprising a surface, wherein the surface is attached to the aptamer of claim 1.

9. A method for detecting the presence of *Legionella pneumophila* in a sample, the method comprises (i) contacting the aptamer of claim 1 with the sample to provide a mixture, (ii) determining the presence of a complex between *Legionella pneumophila* and the aptamer in the mixture and (iii) characterizing the sample as comprising *Legionella pneumophila* if the complex is determined to be present in the mixture.

10. The method of claim 9, wherein the sample is a water sample.

11. The method of claim 9, wherein the sample is a gaseous sample.

12. The method of claim 9, wherein the sample is a biological sample.

13. The method of claim 9, wherein the aptamer is associated with a chromogenic label and step (ii) comprises performing colorimetry for determining the presence of the complex.

14. The method of claim 9, wherein the aptamer is associated with a fluorescent label and step (ii) comprises performing a fluorescent-based assay for determining the presence of the complex.

15. The method of claim 14, wherein the fluorescent-based assay is flow cytometry.

16. The method of claim 14, wherein the fluorescent-based assay is microscopy.

17. The method of claim 9, wherein the aptamer is associated with a radioactive label and step (ii) comprises performing a radioactive-based assay for determining the presence of the complex.

18. The method of claim 9, further comprising determining the viability of *Legionella pneumophila* in the sample.

* * * * *

SEQUENCE LISTING

```
<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: 5' end of library of aptamers
```

<400> SEQUENCE: 1
gcaatggtac ggtacttcc 19

<210> SEQ ID NO 2
<211> LENGTH: 24
<212> TYPE: DNA
<213> ORGANISM: Artificial Sequence
<220> FEATURE:
<223> OTHER INFORMATION: 3'end of library of aptamers

<400> SEQUENCE: 2
caaaagtgca cgctactttg ctaa 24

<210> SEQ ID NO 3
<211> LENGTH: 88
<212> TYPE: DNA
<213> ORGANISM: Artificial Sequence
<220> FEATURE:
<223> OTHER INFORMATION: Library of aptamers
<220> FEATURE:
<221> NAME/KEY: variation
<222> LOCATION: (19)..(64)
<223> OTHER INFORMATION: N = A, T, C or G
<220> FEATURE:
<221> NAME/KEY: misc_feature
<222> LOCATION: (20)..(64)
<223> OTHER INFORMATION: n is a, c, g, or t

<400> SEQUENCE: 3
gcaatggtac ggtacttccn nnnnnnnnnn nnnnnnnnnn nnnnnnnnnn nnnnnnnnnn 60
nnnncaaaag tgcacgctac tttgctaa 88

<210> SEQ ID NO 4
<211> LENGTH: 19
<212> TYPE: DNA
<213> ORGANISM: Artificial Sequence
<220> FEATURE:
<223> OTHER INFORMATION: Forward primer

<400> SEQUENCE: 4
gcaatggtac ggtacttcc 19

<210> SEQ ID NO 5
<211> LENGTH: 24
<212> TYPE: DNA
<213> ORGANISM: Artificial Sequence
<220> FEATURE:
<223> OTHER INFORMATION: Reverse primer

<400> SEQUENCE: 5
ttagcaaagt agcgtgcact tttg 24

<210> SEQ ID NO 6
<211> LENGTH: 88
<212> TYPE: DNA
<213> ORGANISM: Artificial Sequence
<220> FEATURE:
<223> OTHER INFORMATION: Aptamer R6C1

<400> SEQUENCE: 6
gcaatggtac ggtacttccc cactaacgcg cccacgcacc cctcggctac atccagcacc 60
cgcccaaaag tgcacgctac tttgctaa 88

<210> SEQ ID NO 7

-continued

<211> LENGTH: 80
<212> TYPE: DNA
<213> ORGANISM: Artificial Sequence
<220> FEATURE:
<223> OTHER INFORMATION: Aptamer R6C3

<400> SEQUENCE: 7
gcaatggtac ggtacttccc cactccacgc atcacagcct ttcactgccc acgcctcaaa 60
agtgcacgct actttgctaa 80

<210> SEQ ID NO 8
<211> LENGTH: 88
<212> TYPE: DNA
<213> ORGANISM: Artificial Sequence
<220> FEATURE:
<223> OTHER INFORMATION: Aptamer R6C7

<400> SEQUENCE: 8
gcaatggtac ggtacttcca ccaccggagt gtgcttcagc cgtggtacaa tactgccgtg 60
tatccaaaag tgcacgctac tttgctaa 88

<210> SEQ ID NO 9
<211> LENGTH: 87
<212> TYPE: DNA
<213> ORGANISM: Artificial Sequence
<220> FEATURE:
<223> OTHER INFORMATION: Aptamer R6C11

<400> SEQUENCE: 9
gcaatggtac ggtacttccc ccactgcaca cacaaagggc cagcatcaac acacgcgccg 60
ttccaaaagt gcacgctact ttgctaa 87

<210> SEQ ID NO 10
<211> LENGTH: 86
<212> TYPE: DNA
<213> ORGANISM: Artificial Sequence
<220> FEATURE:
<223> OTHER INFORMATION: Aptamer R6C12
<220> FEATURE:
<221> NAME/KEY: misc_feature
<222> LOCATION: (59)..(59)
<223> OTHER INFORMATION: n is a, c, g, or t

<400> SEQUENCE: 10
gcaatggtac ggtacttccc accccgccac gccgatagcc tcccatactc cccccgcang 60
tccaaaagtg cacgctactt tgctaa 86

<210> SEQ ID NO 11
<211> LENGTH: 88
<212> TYPE: DNA
<213> ORGANISM: Artificial Sequence
<220> FEATURE:
<223> OTHER INFORMATION: Aptamer R6C15

<400> SEQUENCE: 11
gcaatggtac ggtacttccc gcgcacccca cacctccgca caccgcatgc ctccccttag 60
gccccaaaag tgcacgctac tttgctaa 88

<210> SEQ ID NO 12
<211> LENGTH: 87
<212> TYPE: DNA
<213> ORGANISM: Artificial Sequence
<220> FEATURE:
<223> OTHER INFORMATION: Aptamer R6C16

<400> SEQUENCE: 12
gcaatggtac ggtacttccc actgccgaac gcgccctctc ctgctgcctc cacacatggt 60
cgccaaaagt gcacgctact ttgctaa 87

<210> SEQ ID NO 13
<211> LENGTH: 89
<212> TYPE: DNA
<213> ORGANISM: Artificial Sequence
<220> FEATURE:
<223> OTHER INFORMATION: Aptamer R6C18

<400> SEQUENCE: 13
gcaatggtac ggtacttccc ccaccaagcc catacacgta cagcctacca caatccacat 60
cgggccaaaa gtgcacgcta ctttgctaa 89

<210> SEQ ID NO 14
<211> LENGTH: 69
<212> TYPE: DNA
<213> ORGANISM: Artificial Sequence
<220> FEATURE:
<223> OTHER INFORMATION: Aptamer R10C5

<400> SEQUENCE: 14
gcaatggtac ggtacttccg gacagtgctg aaaactgtga ccccccaaaa gtgcacgcta 60
ctttgctaa 69

<210> SEQ ID NO 15
<211> LENGTH: 60
<212> TYPE: DNA
<213> ORGANISM: Artificial Sequence
<220> FEATURE:
<223> OTHER INFORMATION: Aptamer R10C1

<400> SEQUENCE: 15
gcaatggtac ggtacttccc caccccacgc tgctcccaaa agtgcacgct actttgctaa 60

<210> SEQ ID NO 16
<211> LENGTH: 26
<212> TYPE: DNA
<213> ORGANISM: Artificial Sequence
<220> FEATURE:
<223> OTHER INFORMATION: Core of aptamer R10C5

<400> SEQUENCE: 16
ggacagtgct gaaaactgtg accccc 26

<210> SEQ ID NO 17
<211> LENGTH: 17
<212> TYPE: DNA
<213> ORGANISM: Artificial Sequence
<220> FEATURE:
<223> OTHER INFORMATION: Core of aptamer R10C1

<400> SEQUENCE: 17
ccaccccacg ctgctcc 17

<210> SEQ ID NO 18
<211> LENGTH: 69
<212> TYPE: DNA
<213> ORGANISM: Artificial Sequence
<220> FEATURE:
<223> OTHER INFORMATION: Scrambled version of aptamer R10C5

-continued

```
<400> SEQUENCE: 18

acagaatcag ttcgagtaca tacgcgcgaa gactcctaag gccgtagcgt tcttcccggt     60

aataccatg                                                              69


<210> SEQ ID NO 19
<211> LENGTH: 60
<212> TYPE: DNA
<213> ORGANISM: Artificial Sequence
<220> FEATURE:
<223> OTHER INFORMATION: Scrambled version of aptamer R10C1

<400> SEQUENCE: 19

tgtactcccg cgtcccacct gctacccgaa atagagtttc cctagaaagg cttgcccaac     60
```